(12) United States Patent  (10) Patent No.: US 7,513,918 B2
Pasquier et al.  (45) Date of Patent: Apr. 7, 2009

(54) AGENTS FOR COLORING KERATIN FIBERS COMPRISING ZWITTERIONIC AZOMETHINE DYES

(75) Inventors: Cécile Pasquier, Marly (CH); Veronique Buclin, Morlon (CH); Anita Roulin, Villarlod (CH); Hans-Jürgen Braun, Ueberstorf (CH)

(73) Assignee: The Procter & Gamble Company, Cincinnati, OH (US)

( * ) Notice: Subject to any disclaimer, the term of this patent is extended or adjusted under 35 U.S.C. 154(b) by 40 days.

(21) Appl. No.: 11/788,065

(22) Filed: Apr. 19, 2007

(65) Prior Publication Data

US 2007/0245501 A1    Oct. 25, 2007

(30) Foreign Application Priority Data

Apr. 19, 2006 (EP) ................... 06008058
Mar. 30, 2007 (EP) ................... 07105282

(51) Int. Cl.
*A61Q 5/10* (2006.01)
*C07D 211/98* (2006.01)

(52) U.S. Cl. ................ 8/405; 8/406; 8/426; 8/435; 8/454; 8/465; 8/566; 8/567; 8/568; 8/570; 8/571; 8/573; 8/574; 546/332

(58) Field of Classification Search ............ 8/405, 8/406, 426, 435, 454, 465, 565, 566, 567, 8/568, 570, 571, 573, 574; 546/332
See application file for complete search history.

(56) References Cited

U.S. PATENT DOCUMENTS 3,573,287 A * 3/1971 Schorr et al. ............. 546/332

FOREIGN PATENT DOCUMENTS

DE         19618595          11/1997
WO      WO-95/01772 A1      1/1995
WO      WO-97/20545 A1      6/1997

OTHER PUBLICATIONS

STIC Search Report dated Jul. 25, 2008.*
International Search Report for PCT/IB2007/051432, Oct. 30, 2007 (5 pages).
European Search Report, Application No. 06008058.7, dated Oct. 6, 2006 (5 pages).

* cited by examiner

*Primary Examiner*—Eisa B Elhilo
(74) *Attorney, Agent, or Firm*—Melissa Krasovec; Marianne Dressman; Tara M. Rosnell

(57) ABSTRACT

The present invention relates to agents for coloring keratin fibers which comprise at least one zwitterionic azomethine dye of the general formula (I), (II), or (III)

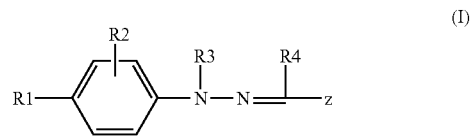

(I)

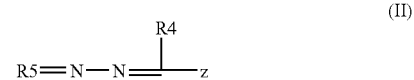

(II)

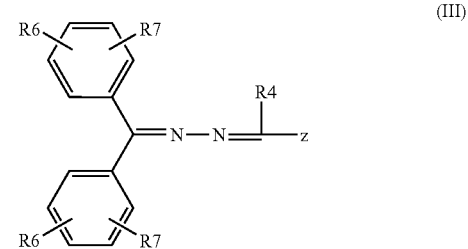

(III)

in which z is a heterocycle of the formula

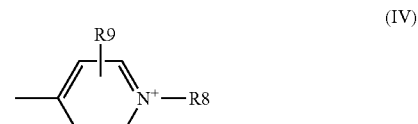

(IV)

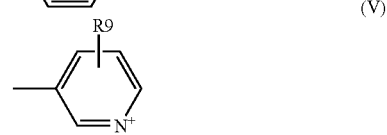

(V)

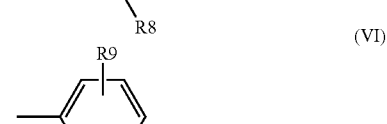

(VI)

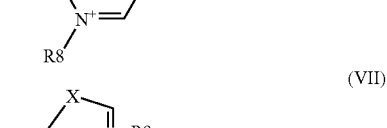

(VII)

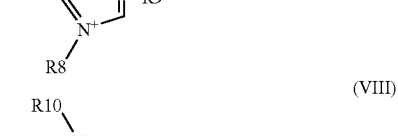

(VIII)

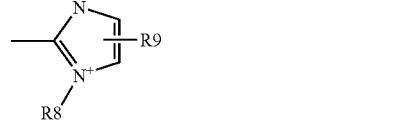

(IX)

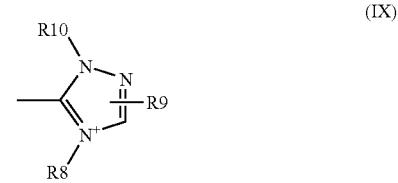

-continued
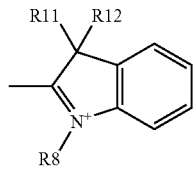
(X)
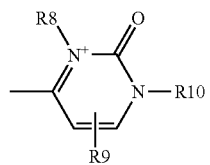
(XI)
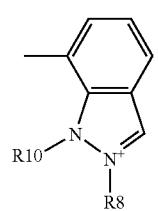
(XII)
in which R8 is an alkyl sulfonate radical of the formula (XIII);
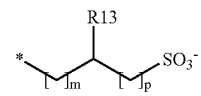
(XIII)
14 Claims, No Drawings

AGENTS FOR COLORING KERATIN FIBERS COMPRISING ZWITTERIONIC AZOMETHINE DYES

FIELD OF THE INVENTION

The present invention relates to agents for coloring keratin fibers, such as, for example, wool, and furs and, in particular, human hair, comprising zwitterionic azomethine dyes.

BACKGROUND OF THE INVENTION

For the color-changing treatment of keratin fibers use is usually made of two coloring methods. In the first method, the coloration is produced with so-called oxidative or permanent colorants using a mixture of various developer substances and coupler substances and an oxidizing agent. If required, in this method, so-called direct (nonoxidative) dyes can be added to round off the coloring result or to produce particular color effects. The second method uses exclusively direct dyes, which are applied to the fibers in a suitable carrier mass. This method is easy to use, exceptionally gentle and is characterized by low damage to keratin fibers. The direct dyes used here are subject to a large number of requirements. For example, they have to be acceptable from a toxicological and dermatological point of view and allow the attainment of colorations in the desired intensity, which, inter alia, also requires adequate solubility in water. In addition, good light-fastness, acid fastness and rubbing fastness are required for the colorations achieved.

Compared with oxidative colorations, nonoxidative colorations, however, generally have lower durability and a poorer root to tip evenness of color. In addition, direct colorants are generally not able to "lighten" the hair since many direct dyes do not withstand the oxidizing agents required for the lightening and/or the required pH of greater than or equal to 9.

WO 95/01772 A1 discloses specific azo dyes and azomethine dyes as well as their use for dyeing keratinic fibers. WO 97/20545 A1 discloses enlightning dyeing compositions for keratinic fibers which contain specific cationic dyes with a —N=N— or —CH=N— group.

U.S. Pat. No. 3,573,287 discloses specific cationic azomethine compounds which are used for controlling infections of the urinary tract.

SUMMARY OF THE INVENTION

It has now been found that certain zwitterionic azomethine or heteroaryl azine dyes intensely color keratin fibers, and are oxidation-stable, and thus can also be used in oxidative coloring systems.

DETAILED DESCRIPTION OF THE INVENTION

The present invention therefore provides:
(a) an agent for the nonoxidative coloring of keratin fibers, in particular human hair;
(b) an agent for the simultaneous lightening and coloring of keratin fibers, in particular human hair, which, besides the dye of the formula (I), (II), or (III), comprises an oxidizing agent; and
(c) an oxidative colorant for keratin fibers, in particular human hair, based on at least one oxidation dye precursor;

where each of the agents (a), (b), and (c) is characterized by comprising at least one zwitterionic azomethine dye of the general formula (I), (II), or (III)

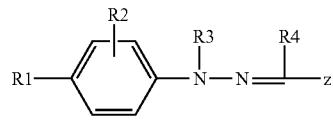

(I)

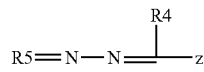

(II)

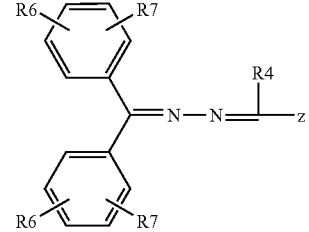

(III)

in which

R1 and R2 may be identical or different and independently of one another, are hydrogen, a halogen atom (F, Cl, Br, I), a saturated or unsaturated ($C_1$-$C_{12}$)-alkyl group, a ($C_1$-$C_{12}$)-alkyl group substituted by a halogen atom (F, Cl, Br, I), a hydroxyl group, a hydroxy-($C_1$-$C_{12}$)-alkyl group, a ($C_1$-$C_{12}$)-alkoxy group, a cyano group, a nitro group, an amino group, a ($C_1$-$C_{12}$)-alkylamino group, a ($C_1$-$C_{12}$)-dialkylamino group, a carboxylic acid group, a C(O)O—($C_1$-$C_{12}$)-alkyl group, a substituted C(O)O-phenyl group or an unsubstituted C(O)O-phenyl group, a substituted phenyl group or an unsubstituted phenyl group, a substituted naphthyl group or an unsubstituted naphthyl group, a substituted heteroaryl group or an unsubstituted heteroaryl group;

R3 is an hydrogen, a saturated or unsaturated ($C_1$-$C_{12}$)-alkyl group, a hydroxy-($C_2$-$C_{12}$)alkyl group, or forms with a carbon atom of the benzene ring a five or six-membered heterocycle which may be substituted with one or more ($C_1$-$C_{12}$)-alkyl group;

R4 is hydrogen, a saturated or unsaturated ($C_1$-$C_{12}$)-alkyl group, a substituted phenyl group or an unsubstituted phenyl group;

R5 is chosen from a group according to the general formula

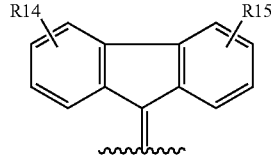

(XIV)

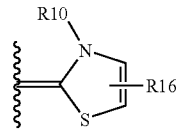

(XV)

-continued

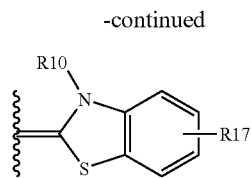
(XVI)

R6 and R7 may be identical or different and, independently of one another, are hydrogen, a halogen atom (F, Cl, Br, I), an amino group, a $(C_1-C_{12})$-alkylamino group, a $(C_1-C_{12})$-dialkylamino group, a $C_1-C_6$-alkylcyano group, a hydroxyl group, a nitro group, a saturated or unsaturated $(C_1-C_{12})$-alkyl group, a hydroxy-$(C_1-C_{12})$-alkyl group, a $(C_1-C_{12})$-alkoxy group, a methoxy-$(C_1-C_{12})$-alkyl group, a C(O)O—$(C_1-C_{12})$-alkyl group;

z is a heterocycle of the formula (IV) to (XII)

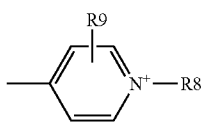
(IV)

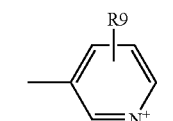
(V)

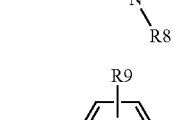
(VI)

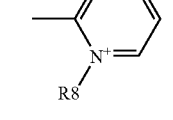
(VII)

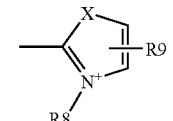
(VIII)

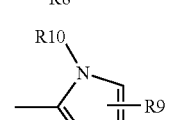
(IX)

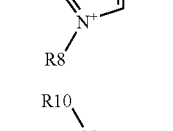
(X)

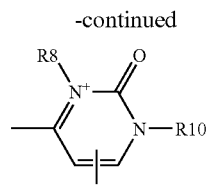
(XI)

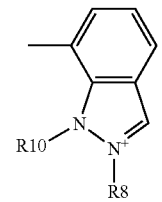
(XII)

X is oxygen or sulfur;
R8 is an alkyl sulfonate radical of the formula (XIII);

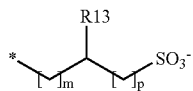
(XIII)

R9 is hydrogen, a halogen atom (F, Cl, Br, I), a saturated or unsaturated $(C_1-C_{12})$-alkyl group, a $(C_1-C_{12})$-alkyl group substituted by a halogen atom (F, Cl, Br, I), a hydroxyl group, a hydroxy-$(C_2-C_{12})$-alkyl group, a $(C_1-C_{12})$-alkoxy group, a cyano group, a nitro group, an amino group, a $(C_1-C_{12})$-alkylamino group, a $(C_1-C_{12})$-dialkylamino group, a carboxylic acid group, a C(O)O—$(C_1-C_{12})$-alkyl group, a substituted or unsubstituted C(O)O-phenyl group, a substituted or unsubstituted phenyl group, or a benzene ring condensed to the heteroaromatic ring of formula (IV) to (XII);

R10 is a saturated or unsaturated $(C_1-C_{12})$-alkyl group or a saturated or unsaturated hydroxy-$(C_1-C_{12})$-alkyl group;

R11 and R12 may be identical or different and independently of one another, are a saturated or unsaturated $(C_1-C_{12})$-alkyl group;

R13 is hydrogen or a hydroxyl group;

R14, R15, R16, and R17 may be identical or different and independently of one another, are hydrogen, a halogen atom (F, Cl, Br, I), a saturated or unsaturated $(C_1-C_{12})$-alkyl group, a $(C_1-C_{12})$-alkyl group substituted by a halogen atom (F, Cl, Br, I), a hydroxyl group, a hydroxy-$(C_1-C_{12})$-alkyl group, a $(C_1-C_{12})$-alkoxy group, a cyano group, a nitro group, an amino group, a $(C_1-C_{12})$-alkylamino group, a $(C_1-C_{12})$-dialkylamino group, a carboxylic acid group, a C(O)O—$(C_1-C_{12})$-alkyl group, a substituted C(O)O-phenyl group or an unsubstituted C(O)O-phenyl group, a substituted phenyl group or an unsubstituted phenyl group, m is equal to 0 to (n−1);
p is equal to 0 to (n−1) with m+p=(n−1) and
n is an integer from 1 to 6.

Among the above mentioned compounds of the formulas (I), (II), and (III), preference is given to those in which n is 2 or 3, and R13 is hydrogen. The most preferred compounds are the compounds of formula (I) in which n is 2 or 3, and R13 is hydrogen.

Examples of suitable compounds of the general formula (I), (II), or (III) that may be mentioned are:

4-(4-{[methyl(phenyl)hydrazono]methyl}-1-pyridiniumyl)-1-butanesulfonate,
4-(3-{[methyl(phenyl)hydrazono]methyl}-1-pyridiniumyl)-1-butanesulfonate,
4-(2-{[methyl(phenyl)hydrazono]methyl}-1-pyridiniumyl)-1-butanesulfonate,
4-(4-{[(4-methoxyphenyl)(methyl)hydrazono]methyl}-1-pyridiniumyl)-1-butanesulfonate,
4-(3-{[(4-methoxyphenyl)(methyl)hydrazono]methyl}-1-pyridiniumyl)-1-butanesulfonate,
4-(2-{[(4-methoxyphenyl)(methyl)hydrazono]methyl}-1-pyridiniumyl)-1-butanesulfonate,
4-(4-{[(2-methoxyphenyl)(methyl)hydrazono]methyl}-1-pyridiniumyl)-1-butanesulfonate,
4-(3-{[(2-methoxyphenyl)(methyl)hydrazono]methyl}-1-pyridiniumyl)-1-butanesulfonate,
4-(2-{[(2-methoxyphenyl)(methyl)hydrazono]methyl}-1-pyridiniumyl)-1-butanesulfonate,
4-(4-{[(4-hydroxyphenyl)(methyl)hydrazono]methyl}-1-pyridiniumyl)-1-butanesulfonate,
4-(3-{[(4-hydroxyphenyl)(methyl)hydrazono]methyl}-1-pyridiniumyl)-1-butanesulfonate,
4-(2-{[(4-hydroxyphenyl)(methyl)hydrazono]methyl}-1-pyridiniumyl)-1-butanesulfonate,
4-(4-{[methyl(4-methylphenyl)hydrazono]methyl}-1-pyridiniumyl)-1-butanesulfonate,
4-(3-{[methyl(4-methylphenyl)hydrazono]methyl}-1-pyridiniumyl)-1-butanesulfonate,
4-(2-{[methyl(4-methylphenyl)hydrazono]methyl}-1-pyridiniumyl)-1-butanesulfonate,
4-(4-{[(4-chlorophenyl)(methyl)hydrazono]methyl}-1-pyridiniumyl)-1-butanesulfonate,
4-(3-{[(4-chlorophenyl)(methyl)hydrazono]methyl}-1-pyridiniumyl)-1-butanesulfonate,
4-(2-{[(4-chlorophenyl)(methyl)hydrazono]methyl}-1-pyridiniumyl)-1-butanesulfonate,
4-(4-{[methyl(4-nitrophenyl)hydrazono]methyl}-1-pyridiniumyl)-1-butanesulfonate,
4-(3-{[methyl(4-nitrophenyl)hydrazono]methyl}-1-pyridiniumyl)-1-butanesulfonate,
4-(2-{[methyl(4-nitrophenyl)hydrazono]methyl}-1-pyridiniumyl)-1-butanesulfonate,
4-{4-[(phenylhydrazono)methyl]-1-pyridiniumyl}-1-butanesulfonate,
4-{3-[(phenylhydrazono)methyl]-1-pyridiniumyl}-1-butanesulfonate,
4-{2-[(phenylhydrazono)methyl]-1-pyridiniumyl}-1-butanesulfonate,
4-(4-{[(4-methoxyphenyl)hydrazono]methyl}-1-pyridiniumyl)-1-butanesulfonate,
4-(3-{[(4-methoxyphenyl)hydrazono]methyl}-1-pyridiniumyl)-1-butanesulfonate,
4-(2-{[(4-methoxyphenyl)hydrazono]methyl}-1-pyridiniumyl)-1-butanesulfonate,
4-{4-[N-methyl-N-phenylethanehydrazonoyl]-1-pyridiniumyl}-1-butanesulfonate,
4-{3-[N-methyl-N-phenylethanehydrazonoyl]-1-pyridiniumyl}-1-butanesulfonate,
4-{2-[N-methyl-N-phenylethanehydrazonoyl]-1-pyridiniumyl}-1-butanesulfonate,
4-{4-[N-phenylethanehydrazonoyl]-1-pyridiniumyl}-1-butanesulfonate,
4-{3-[N-phenylethanehydrazonoyl]-1-pyridiniumyl}-1-butanesulfonate,
4-{2-[N-phenylethanehydrazonoyl]-1-pyridiniumyl}-1-butanesulfonate,
4-(2-{[methyl(phenyl)hydrazono]methyl}-1,3-thiazol-3-ium-3-yl)-1-butanesulfonate,
4-(1-methyl-2-{[methyl(phenyl)hydrazono]methyl}-1H-imidazol-3-ium-3-yl)-1-butanesulfonate,
4-(2-{[methyl(phenyl)hydrazono]methyl}-1,3-oxazol-3-ium-3-yl)-1-butanesulfonate,
4-(4-methyl-5-{[methyl(phenyl)hydrazono]methyl}-4H-1,2,4-triazol-1-ium-1-yl)-1-butanesulfonate,
4-(4-{[methyl(phenyl)hydrazono]methyl}-1-quinoliniumyl)-1-butanesulfonate,
4-(2-{[methyl(phenyl)hydrazono]methyl}-1-quinoliniumyl)-1-butanesulfonate,
4-{4-[(2,3-dihydro-1H-indol-1-ylimino)methyl]-1-pyridiniumyl}-1-butanesulfonate,
4-(4-{[(2,2,3,3-tetramethyl-2,3-dihydro-1H-indol-1-yl)imino]methyl}-1-pyridiniumyl)-1-butanesulfonate,
4-(3,3-dimethyl-2-{[methyl(phenyl)hydrazono]methyl}-3H-indolium-1-yl)-1-butanesulfonate,
4-(2-{[(4-methoxyphenyl)(methyl)hydrazono]methyl}-3,3-dimethyl-3H-indolium-1-yl)-1-butanesulfonate,
4-(3-methyl-6-{[methyl(phenyl)hydrazono]methyl}-2-oxo-2,3-dihydropyrimidin-1-ium-1-yl)-1-butanesulfonate,
4-(1-methyl-7-{[methyl(phenyl)hydrazono]methyl}-1H-indazol-2-ium-2-yl)-1-butanesulfonate,
3-(4-{[methyl (phenyl)hydrazono]methyl}-1-pyridiniumyl)-1-propanesulfonate,
3-(3-{[methyl(phenyl)hydrazono]methyl}-1-pyridiniumyl)-1-propanesulfonate,
3-(2-{[methyl(phenyl)hydrazono]methyl}-1-pyridiniumyl)-1-propanesulfonate,
3-(4-{[(4-methoxyphenyl)(methyl)hydrazono]methyl}-1-pyridiniumyl)-1-propanesulfonate,
3-(3-{[(4-methoxyphenyl)(methyl)hydrazono]methyl}-1-pyridiniumyl)-1-propanesulfonate,
3-(2-{[(4-methoxyphenyl)(methyl)hydrazono]methyl}-1-pyridiniumyl)-1-propanesulfonate,
3-(4-{[(2-methoxyphenyl)(methyl)hydrazono]methyl}-1-pyridiniumyl)-1-propanesulfonate,
3-(3-{[(2-methoxyphenyl)(methyl)hydrazono]methyl}-1-pyridiniumyl)-1-propanesulfonate,
3-(2-{[(2-methoxyphenyl)(methyl)hydrazono]methyl}-1-pyridiniumyl)-1-propanesulfonate,
3-(4-{[(4-hydroxyphenyl)(methyl)hydrazono]methyl}-1-pyridiniumyl)-1-propanesulfonate,
3-(3-{[(4-hydroxyphenyl)(methyl)hydrazono]methyl}-1-pyridiniumyl)-1-propanesulfonate,
3-(2-{[(4-hydroxyphenyl)(methyl)hydrazono]methyl}-1-pyridiniumyl)-1-propanesulfonate,
3-(4-{[methyl(4-methylphenyl)hydrazono]methyl}-1-pyridiniumyl)-1-propanesulfonate,
3-(3-{[methyl(4-methylphenyl)hydrazono]methyl}-1-pyridiniumyl)-1-propanesulfonate,
3-(2-{[methyl(4-methylphenyl)hydrazono]methyl}-1-pyridiniumyl)-1-propanesulfonate,
3-(4-{[(4-chlorophenyl)(methyl)hydrazono]methyl}-1-pyridiniumyl)-1-propanesulfonate,
3-(3-{[(4-chlorophenyl)(methyl)hydrazono]methyl}-1-pyridiniumyl)-1-propanesulfonate,
3-(2-{[(4-chlorophenyl)(methyl)hydrazono]methyl}-1-pyridiniumyl)-1-propanesulfonate,
3-(4-{[methyl(4-nitrophenyl)hydrazono]methyl}-1-pyridiniumyl)-1-propanesulfonate,
3-(3-{[methyl(4-nitrophenyl)hydrazono]methyl}-1-pyridiniumyl)-1-propanesulfonate,
3-(2-{[methyl(4-nitrophenyl)hydrazono]methyl}-1-pyridiniumyl)-1-propanesulfonate, 3-{4-[(phenylhydrazono)methyl]-1-pyridiniumyl}-1-propanesulfonate,
3-{3-[(phenylhydrazono)methyl]-1-pyridiniumyl}-1-propanesulfonate,
3-{2-[(phenylhydrazono)methyl]-1-pyridiniumyl}-1-propanesulfonate,
3-(4-{[(4-methoxyphenyl)hydrazono]methyl}-1-pyridiniumyl)-1-propanesulfonate,
3-(3-{[(4-methoxyphenyl)hydrazono]methyl}-1-pyridiniumyl)-1-propanesulfonate,
3-(2-{[(4-methoxyphenyl)hydrazono]methyl}-1-pyridiniumyl)-1-propanesulfonate,
3-{4-[N-methyl-N-phenylethanehydrazonoyl]-1-pyridiniumyl}-1-propanesulfonate,
3-{3-[N-methyl-N-phenylethanehydrazonoyl]-1-pyridiniumyl}-1-propanesulfonate,
3-{2-[N-methyl-N-phenylethanehydrazonoyl]-1-pyridiniumyl}-1-propanesulfonate,
3-{4-[N-phenylethanehydrazonoyl]-1-pyridiniumyl}-1-propanesulfonate,
3-{3-[N-phenylethanehydrazonoyl]-1-pyridiniumyl}-1-propanesulfonate,
3-{2-[N-phenylethanehydrazonoyl]-1-pyridiniumyl}-1-propanesulfonate,
3-(2-{[methyl(phenyl)hydrazono]methyl}-1,3-thiazol-3-ium-3-yl)-1-propanesulfonate,
3-(1-methyl-2-{[methyl(phenyl)hydrazono]methyl}-1H-imidazol-3-ium-3-yl)-1-propanesulfonate,
3-(2-{[methyl(phenyl)hydrazono]methyl}-1,3-oxazol-3-ium-3-yl)-1-propanesulfonate,
3-(4-methyl-5-{[methyl(phenyl)hydrazono]methyl}-4H-1,2,4-triazol-1-ium-1-yl)-1-propanesulfonate,
3-(4-{[methyl(phenyl)hydrazono]methyl}-1-quinoliniumyl)-1-propanesulfonate,
3-(2-{[methyl(phenyl)hydrazono]methyl}-1-quinoliniumyl)-1-propanesulfonate,
3-{4-[(2,3-dihydro-1H-indol-1-ylimino)methyl]-1-pyridiniumyl}-1-propanesulfonate
3-(4-{[(2,2,3,3-tetramethyl-2,3-dihydro-1H-indol-1-yl)imino]methyl}-1-pyridiniumyl)-1-propanesulfonate,
3-(3,3-dimethyl-2-{[methyl(phenyl)hydrazono]methyl}-3H-indolium-1-yl)-1-propanesulfonate,
3-(2-{[(4-methoxyphenyl)(methyl)hydrazono]methyl}-3,3-dimethyl-3H-indolium-1-yl)-1-propanesulfonate,
3-(3-methyl-6-{[methyl(phenyl)hydrazono]methyl}-2-oxo-2,3-dihydropyrimidin-1-ium-1-yl)-1-propanesulfonate,
3-(1-methyl-7-{[methyl(phenyl)hydrazono]methyl}-1H-indazol-2-ium-2-yl)-1-propanesulfonate,
4-(4-{[(3-methyl-1,3-benzothiazol-2(3H)-ylidene)hydrazono]methyl}-1-pyridiniumyl)-1-butanesulfonate,
4-(3-{[(3-methyl-1,3-benzothiazol-2(3H)-ylidene)hydrazono]methyl}-1-pyridiniumyl)-1-butanesulfonate,
4-(4-{[(3,4-dimethyl-1,3-thiazol-2(3H)-ylidene)hydrazono]methyl}-1-pyridiniumyl)-1-butanesulfonate,
4-(3-{[(3,4-dimethyl-1,3-thiazol-2(3H)-ylidene)hydrazono]methyl}-1-pyridiniumyl)-1-butanesulfonate,
4-(4-{[(3,4,5-trimethyl-1,3-thiazol-2(3H)-ylidene)hydrazono]methyl}-1-pyridiniumyl)-1-butanesulfonate,
4-(3-{[(3,4,5-trimethyl-1,3-thiazol-2(3H)-ylidene)hydrazono]methyl}-1-pyridiniumyl)-1-butanesulfonate,
4-(1-methyl-2-{[2-(3-methyl-1,3-benzothiazol-2(3H)-ylidene)hydrazono]methyl}-1H-imidazol-3-ium-3-yl)-1-butanesulfonate,
4-(2-{[2-(3,4-dimethyl-1,3-thiazol-2(3H)-ylidene)hydrazono]methyl}-1-methyl-1H-imidazol-3-ium-3-yl)-1-butanesulfonate,
4-(2-{[2-(3,4,5-trimethyl-1,3-thiazol-2(3H)-ylidene)hydrazono]methyl}-1-methyl-1H-imidazol-3-ium-3-yl)-1-butanesulfonate,
4-{4-[({bis[4-(dimethylamino)phenyl]methylene}hydrazono)methyl]-1-pyridiniumyl}-1-butanesulfonate,
4-{3-[({bis[4-(dimethylamino)phenyl]methylene}hydrazono)methyl]-1-pyridiniumyl}-1-butanesulfonate,
4-{4-[(9H-fluoren-9-ylidenehydrazono)methyl]-1-pyridiniumyl}-1-butanesulfonate,
4-{4-[({bis[4-(dimethylamino)phenyl]methylene}hydrazono)methyl]-1-quinoliniumyl}-1-butanesulfonate,
3-(4-{[(3-methyl-1,3-benzothiazol-2(3H)-ylidene)hydrazono]methyl}-1-pyridiniumyl)-1-propanesulfonate,
3-(3-{[(3-methyl-1,3-benzothiazol-2(3H)-ylidene)hydrazono]methyl}-1-pyridiniumyl)-1-propanesulfonate,
3-(4-{[(3,4-dimethyl-1,3-thiazol-2(3H)-ylidene)hydrazono]methyl}-1-pyridiniumyl)-1-propanesulfonate,
3-(3-{[(3,4-dimethyl-1,3-thiazol-2(3H)-ylidene)hydrazono]methyl}-1-pyridiniumyl)-1-propanesulfonate,
3-(4-{[(3,4,5-trimethyl-1,3-thiazol-2(3H)-ylidene)hydrazono]methyl}-1-pyridiniumyl)-1-propanesulfonate,
3-(3-{[(3,4,5-trimethyl-1,3-thiazol-2(3H)-ylidene)hydrazono]methyl}-1-pyridiniumyl)-1-propanesulfonate,
3-(1-methyl-2-{[2-(3-methyl-1,3-benzothiazol-2(3H)-ylidene)hydrazono]methyl}-1H-imidazol-3-ium-3-yl)-1-propanesulfonate,
3-(2-{[2-(3,4-dimethyl-1,3-thiazol-2(3H)-ylidene)hydrazono]methyl}-1-methyl-1H-imidazol-3-ium-3-yl)-1-propanesulfonate,
3-(2-{[2-(3,4,5-trimethyl-1,3-thiazol-2(3H)-ylidene)hydrazono]methyl}-1-methyl-1H-imidazol-3-ium-3-yl)-1-propanesulfonate,
3-{4-[({bis[4-(dimethylamino)phenyl]methylene}hydrazono)methyl]-1-pyridiniumyl}-1-propanesulfonate,
3-{3-[({bis[4-(dimethylamino)phenyl]methylene}hydrazono)methyl]-1-pyridiniumyl}-1-propanesulfonate,
3-{4-[(9H-fluoren-9-ylidenehydrazono)methyl]-1-pyridiniumyl}-1-propanesulfonate and
3-{4-[({bis[4-(dimethylamino)phenyl]methylene}hydrazono)methyl]-1-quinoliniumyl}-1-propanesulfonate.

The dyes of the formula (I), (II), and (III) are present in the colorant according to the invention preferably in a total amount of from about 0.01% to about 10% by weight, in particular about 0.1% to about 8% by weight.

To extend the color pallet, the colorant (a) according to the invention besides the dyes of the formula (I), may additionally also comprise further known direct synthetic dyes from the group consisting of nitro dyes, azo dyes, anthraquinone dyes, triphenylmethane dyes and basic or acidic dyes, and natural direct dyes, alone or in a mixture with one another.

The colorant (b) according to the invention, which is characterized by a content of an oxidizing agent, preferably hydrogen peroxide, besides the dyes of the general formula (I) may additionally also comprise further oxidation-stable direct dyes, such as, for example, 3-(2',6'-diaminopyridyl-3'-azo)pyridine (=2,6-diamino-3-((pyridin-3-yl)azo)pyridine), N,N-di(2-hydroxyethyl)-3-methyl-4-((4-nitrophenyl)azo)aniline (Disperse Red 17, CI1210), 3-diethylamino-7-(4-dimethylaminophenylazo)-5-phenylphenazinium chloride (Cl11050), 4-(2-thiazolylazo)resorcinol, 4-((4-phenylamino)azo)benzosulfonic acid sodium salt (Orange IV), 1-((3-aminopropyl)amino)-9,10-anthracenedione (HC Red No. 8), 3',3",4,5,5',5",6,7-octabromophenol sulfonephthalein (tetrabromophenol Blue), 1-((4-amino-3,5-dimethylphenyl)(2,6-dichlorophenyl)methylene)-3,5-dimethyl-4-imino-2,5-cyclohexadiene-phosphoric acid (1:1) (Basic Blue 77), 3',3",5', 5"-tetrabromo-m-cresol sulfonephthalein, 2,4-dinitro-1-naphthol-7-sulfonic acid disodium salt (Acid Yellow 1, CI 10316), 4-[2'-hydroxy-1'-naphthyl)azo]benzosulfonic acid sodium salt (Acid Orange 7, CI15510), 3',6'-dihydroxy-2',4', 5',7'-tetraiodospiro[isobenzofuran-1(3H), 9'-(9H)xanthen]-3-one disodium salt (Acid Red 51, Cl45430), 6-hydroxy-5-((2-methoxy-5-methyl-4-sulfophenyl)azo)-2-naphthalenesulfonic acid disodium salt (FD&C Red 40, Cl16035), 2,4-dinitro-1-naphthol sodium salt (Acid Yellow 24; Cl10315), 2',4',5',7'-tetrabromo-4,5,6,7-tetrachloro-3',6'-dihydroxyspiro(isobenzofuran-1(3H), 9'-[9H]xanthen]-3-one disodium salt (Acid Red 92; Cl45410), 4-(2-hydroxy-1-naphthylazo)-3-methylbenzenesulfonic acid sodium salt (Acid Orange 8, CI15575), 2-amino-1,4-naphthalenedione, dithizone (1,5-diphenylthiocarbazone), N-((2-hydroxyethyl)-2-nitro-4-trifluoromethyl)aniline (HC Yellow 13), N-(2-hydroxyethyl)-4-nitroaniline and 4-chloro-N-(2,3-dihydroxypropyl)-2-nitroaniline, 1-methyl-4-((methylphenyl-hydrazono)methyl)pyridinium methylsulfate (Basic Yellow No. 87), 3-((4,5-dihydro-3-methyl-5-oxo-1-phenyl-1H-pyrazol-4-yl)azo)-N,N,N-trimethylbenzenaminium chloride, 3-[(3-methyl-5-hydroxy-1-phenyl-1H-pyrazol-4-yl) azo]-trimethylammoniobenzene chloride (Basic Yellow No. 57), 2-((4-aminophenyl)azo)-1,3-dimethyl-1H-imidazol-3-ium chloride (Basic Orange No. 31), 1,4-dimethyl-5-[(4-(dimethylamino)phenyl)azo]-1,2,4-triazolium chloride (Basic Red No. 22, CI11055), 2-((4-(dimethylamino)-phenyl) azo)-1,3-dimethyl-1H-imidazolium chloride (Basic Red No. 51), 1,4-dimethyl-5-[[4-[methyl(phenylmethyl)amino]phenyl]-azo]-1,2,4-triazolium bromide (Basic Red No. 46), N,N, N-trimethyl-3-{[4-(methylamino)-9,10-dioxo-9,10-dihydro-1-anthracenyl]amino}-1-propanaminium methylsulfate, N,N-dimethyl-3-{[4-(methylamino)-9,10-dioxo-9,10-dihydro-1-anthracenyl]amino}-N-propyl-1-propanaminium chloride and N,N-dimethyl-3-{[4-(methylamino)-9,10-dioxo-9,10-dihydro-1-anthracenyl]amino}-N-propyl-1-propanaminium bromide.

The total content of additional dyes in the colorant according to the invention is about 0.01% to about 15% by weight, in particular about 0.1% to about 12% by weight.

The oxidation colorant (c) according to the invention which is mixed prior to application with an oxidizing agent (in particular hydrogen peroxide or its addition compounds) comprises, besides the dyes of the general formula (I), oxidation dye precursors and if necessary one or more of the abovementioned direct dyes, provided these direct dyes are stable to the oxidizing agent used.

Suitable oxidation dye precursors which may be specified are, for example, the following developer substances and coupler substances and self-coupling compounds:

(i) Developer substances: 1,4-diaminobenzene (p-phenylenediamine), 1,4-diamino-2-methylbenzene (p-tolylenediamine), 1,4-diamino-2,6-dimethylbenzene, 1,4-diamino-3,5-diethylbenzene, 1,4-diamino-2,5-dimethylbenzene, 1,4-diamino-2,3-dimethylbenzene, 2-chloro-1,4-diaminobenzene, 1,4-diamino-2-(thiophen-2-yl)benzene, 1,4-diamino-2-(thiophen-3-yl)benzene, 1,4-diamino-2-(pyridin-3-yl)benzene, 2,5-diaminobiphenyl, 1,4-diamino-2-methoxymethylbenzene, 1,4-diamino-2-aminomethylbenzene, 1,4-diamino-2-hydroxymethylbenzene, 1,4-diamino-2-(2-hydroxyethoxy)benzene, 2-(2-(acetylamino)ethoxy)-1, 4-diaminobenzene, 4-phenylaminoaniline, 4-dimethylaminoaniline, 4-diethylaminoaniline, 4-dipropylaminoaniline, 4-[ethyl(2-hydroxyethyl)-amino]aniline, 4-[di(2-hydroxyethyl)amino]aniline, 4-[di(2-hydroxyethyl)-amino]-2-methylaniline, 4-[(2-methoxyethyl)amino]aniline, 4-[(3-hydroxypropyl)amino]aniline, 4-[(2,3-dihydroxypropyl)amino]aniline, 1,4-diamino-2-(2-hydroxyethyl)benzene, 1,4-diamino-2-(1-methylethyl)-benzene, 1,3-bis[(4-aminophenyl)(2-hydroxyethyl)amino]-2-propanol, 1,4-bis[(4-aminophenyl)amino]butane, 1,8-bis(2,5-diaminophenoxy)-3,6-dioxaoctane, 4-aminophenol, 4-amino-3-methylphenol, 4-amino-3-(hydroxymethyl)phenol, 4-amino-3-fluorophenol, 4-methylaminophenol, 4-amino-2-(aminomethyl)phenol, 4-amino-2-(hydroxymethyl)phenol, 4-amino-2-fluorophenol, 4-amino-2-[(2-hydroxyethyl)amino] methylphenol, 4-amino-2-methylphenol, 4-amino-2-(methoxymethyl)phenol, 4-amino-2-(2-hydroxyethyl) phenol, 5-aminosalicylic acid, 2,5-diaminopyridine, 2,4,5,6-tetraminopyrimidine, 2,5,6-triamino-4-(1H)-pyrimidone, 4,5-diamino-1-(2-hydroxyethyl)-1H-pyrazole, 4,5-diamino-1-(1-methylethyl)-1H-pyrazole, 4,5-diamino-1-[(4-methylphenyl)methyl]-1H-pyrazole, 1-[(4-chlorophenyl)methyl]-4,5-diamino-1H-pyrazole, 4,5-diamino-1-methyl-1H-pyrazole, 2-aminophenol, 2-amino-6-methylphenol, 2-amino-5-methylphenol, alone or in a mixture with one another.

(ii) Coupler substances: N-(3-dimethylaminophenyl)urea, 2,6-diaminopyridine, 2-amino-4-[(2-hydroxyethyl)amino] anisole, 2,4-diamino-1-fluoro-5-methylbenzene, 2,4-diamino-1-methoxy-5-methylbenzene, 2,4-diamino-1-ethoxy-5-methylbenzene, 2,4-diamino-1-(2-hydroxyethoxy)-5-methylbenzene, 2,4-di[(2-hydroxyethyl)amino]-1,5-dimethoxybenzene, 2,3-diamino-6-methoxypyridine, 3-amino-6-methoxy-2-(methylamino)pyridine, 2,6-diamino-3,5-dimethoxypyridine, 3,5-diamino-2,6-dimethoxypyridine, 1,3-diaminobenzene, 2,4-diamino-1-(2-hydroxyethoxy)benzene, 1,3-diamino-4-(2,3-dihydroxypropoxy) benzene, 2,4-diamino-1,5-di(2-hydroxyethoxy)benzene, 1-(2-aminoethoxy)-2,4-diaminobenzene, 2-amino-1-(2-hydroxyethoxy)-4-methylaminobenzene, 2,4-diaminophenoxyacetic acid, 3-[di(2-hydroxyethyl)amino]aniline, 4-amino-2-di[(2-hydroxyethyl)amino]-1-ethoxybenzene, 5-methyl-2-(1-methylethyl)phenol, 3-[(2-hydroxyethyl) amino]aniline, 3-[(2-aminoethyl)-amino]aniline, 1,3-di(2,4-diaminophenoxy)propane, di(2,4-diamino-phenoxy)methane, 1,3-diamino-2,4-dimethoxybenzene, 2,6-bis(2-hydroxyethyl)aminotoluene, 4-hydroxyindole, 3-dimethylaminophenol, 3-diethylaminophenol, 5-amino-2-methylphenol, 5-amino-4-fluoro-2-methylphenol, 5-amino-4-methoxy-2-methylphenol, 5-amino-4-ethoxy-2-methylphenol, 3-amino-2,4-dichlorophenol, 5-amino-2,4-dichlorophenol, 3-amino-2-methylphenol, 3-amino-2-chloro-6-methylphenol, 3-aminophenol, 2-[(3-hydroxyphenyl)amino]acetamide, 5-[(2-hydroxyethyl) amino]-4-methoxy-2-methylphenol, 5-[(2-hydroxyethyl)-amino]-2-methylphenol, 3-[(2-hydroxyethyl)amino]phenol, 3-[(2-methoxyethyl)amino]phenol, 5-amino-2-ethylphenol, 5-amino-2-methoxyphenol, 2-(4-amino-2-hydroxyphenoxy) ethanol, 5-[(3-hydroxypropyl)amino]-2-methylphenol, 3-[(2,3-dihydroxypropyl)-amino]-2-methylphenol, 3-[(2-hydroxyethyl)amino]-2-methylphenol, 2-amino-3-hydroxypyridine, 5-amino-4-chloro-2-methylphenol, 1-naphthol, 2-methyl-1-naphthol, 1,5-dihydroxynaphthalene, 1,7-dihydroxy-naphthalene, 2,3-dihydroxynaphthalene, 2,7-dihydroxynaphthalene, 2-methyl-1-naphthol acetate, 1,3-dihydroxybenzene, 1-chloro-2,4-dihydroxybenzene, 2-chloro-1, 3-dihydroxybenzene, 1,2-dichloro-3,5-dihydroxy-4-methylbenzene, 1,5-dichloro-2,4-dihydroxybenzene, 1,3-dihydroxy-2-methylbenzene, 3,4-methylenedioxyphenol, 3,4-methylenedioxyaniline, 5-[(2-hydroxyethyl)amino]-1,3-benzodioxol, 6-bromo-1-hydroxy-3,4-methylenedioxybenzene, 3,4-diaminobenzoic acid, 3,4-dihydro-6-hydroxy-1,4 (2H)-benzoxazine, 6-amino-3,4-dihydro-1,4(2H)-benzoxazine, 3-methyl-1-phenyl-5-pyrazolone, 5,6-dihydroxyindole, 5,6-dihydroxyindoline, 5-hydroxyindole, 6-hydroxyindole, 7-hydroxyindole, 2,3-indolenedione, alone or in a mixture with one another.

(iii) Self-coupling compounds: 2-amino-5-methylphenol, 2-amino-5-ethylphenol, 2-amino-6-methylphenol, 2-amino-5-ethoxyphenol or 2-propylamino-5-aminopyridine.

The total amount of the oxidation dye precursors present in the colorant (c) according to the invention is from about 0.01% to about 12% by weight, in particular from about 0.2% to about 6% by weight.

To increase the color intensity, the carriers customary used in cosmetic systems can be added if required. Suitable compounds are described, for example, in German Patent No. 196 18 595, which is herewith expressly included by reference. Particularly suitable carriers are, for example, benzyl alcohol, vanillin and isovanillin.

For coloring, the dyes described above are applied in a suitable color carrier mass.

The colorant (a), (b), or (c) according to the invention can also comprise all additives customary and known for such preparations, for example perfume oils, complexing agents, waxes, preservatives, thickeners, antioxidants, alginates, guar gum, haircare substances, such as, for example, cationic polymers or lanolin derivatives, or anionic, nonionic, amphoteric or cationic surface-active substances. Preference is given to using amphoteric or nonionic surface-active substances, for example betaine surfactants, propionates and glycinates, such as, for example, cocoamphoglycinates or cocoamphodiglycinates, ethoxylated surfactants with 1 ethylene oxide unit to 1000 ethylene oxide units, preferably with 1 ethylene oxide unit to 300 ethylene oxide units, such as, for example, glyceride alkoxylates, for example, castor oil ethoxylated with 25 ethylene oxide units, polyglycolamides, ethoxylated alcohols and ethoxylated fatty alcohols (fatty alcohol alkoxylates) and ethoxylated fatty acid sugar esters, in particular ethoxylated sorbitan fatty acid esters. The abovementioned constituents are used in the amounts customary for such purposes, for example, the surface-active substances in a concentration of from about 0.1% to about 30% by weight, and the care substances in an amount of from about 0.1% to about 5% by weight.

The colorant (a), (b), or (c) according to the invention, particularly if it is a hair colorant, can be present in the form of a powder or granules which is/are dissolved prior to application in an aqueous or aqueous-alcoholic preparation, or else in the form of an aqueous or aqueous-alcoholic solution, a cream, a gel, an emulsion, or an aerosol foam, where the colorant can be formulated either in the form of a single-component preparation or else in the form of a multicomponent preparation, for example, in the form of a two-component preparation in which the particular dye derivative of the general formula (I) is packaged separately from the other constituents and the ready-to-use colorant is only prepared directly prior to application by mixing the two components.

The colorant (a), (b), or (c) according to the invention generally has a pH of from about 2 to about 11, preferably from about 5 to about 10. Both organic and inorganic acids or bases are suitable for adjusting the pH according to the invention.

Examples of suitable acids are, in particular, the following acids: α-hydroxycarboxylic acids, such as, for example, glycolic acid, lacetic acid, tartaric acid, citric acid or malic acid, ascorbic acid, gluconic acid lactone, acetic acid, hydrochloric acid or phosphoric acid, and mixtures of these acids.

Examples of suitable bases are, in particular, sodium carbonate, sodium hydrogencarbonate, organic amines, for example monoethanolamine, triethanolamine, 2-amino-2-methyl-1-propanol or tris(hydroxymethyl)aminomethane, ammonia, potassium hydroxide or sodium hydroxide, and mixtures thereof.

Depending on the intended use, the colorant according to the invention can be used with one or more oxidizing agents (lightening; oxidation colorants) or without an oxidizing agent (nonoxidative colorants).

The compositions according to the present invention may comprise at least one source of an oxidizing agent for developing the hair color. Preferred oxidizing agents for use herein are water-soluble peroxygen oxidizing agents. "Water-soluble" as defined herein means that in standard condition at least 0.1 g, preferably about 1 g, more preferably about 10 g of said oxidizing agent can be dissolved in 1 liter of deionized water. The oxidizing agents are valuable for the initial solubilisation and decolorisation of the melanin (bleaching) and accelerate the oxidation of the oxidative dye precursors (oxidative dyeing) in the hair shaft.

Any oxidizing agent known in the art may be utilized in the present invention. Preferred water-soluble oxidizing agents are inorganic peroxygen materials capable of yielding hydrogen peroxide in an aqueous solution. Water-soluble peroxygen oxidizing agents are well known in the art and include hydrogen peroxide, inorganic alkali metal peroxides such as sodium periodate and sodium peroxide and organic peroxides such as urea peroxide, melamine peroxide, and inorganic perhydrate salt bleaching compounds, such as the alkali metal salts of perborates, percarbonates, perphosphates, persilicates, persulphates, and the like. These inorganic perhydrate salts may be incorporated as monohydrates, tetrahydrates, etc. Alkyl and aryl peroxides, and or peroxidases may also be used. Mixtures of two or more such oxidizing agents can also be used if desired. The oxidizing agents may be provided in aqueous solution or as a powder which is dissolved prior to use. Preferred for use in the compositions according to the present invention are hydrogen peroxide, percarbonate, persulphates, and combinations thereof.

According to the present invention the compositions comprise from about 0.1% to about 15% by weight, preferably from about 1% to about 10% by weight, and most preferably from about 2% to about 7% by weight of an oxidizing agent.

Another preferred oxidizing agent for use herein is a source of peroxymonocarbonate ions. Preferably such a source is formed in situ from a source of hydrogen peroxide and a hydrogen carbonate ion source. Such an oxidizing agent has been found to be particularly effective at a pH of up to and including 9.5, preferably 7.5 to 9.5 more preferably about pH 9. Moreover, this system is also particularly effective in combination with a source of ammonia or ammonium ions. It has been found that this oxidizing agent can deliver improvements to the desired hair color results particularly with regard to the delivery of high lift, while considerably reducing the odor, skin and scalp irritation, and damage to the hair fibers.

Accordingly, any source of these ions may be utilized. Suitable sources for use herein include sodium, potassium, guanidine, arginine, lithium, calcium, magnesium, barium, ammonium salts of carbonate, carbamate and hydrocarbonate ions and mixtures thereof such as sodium carbonate, sodium hydrogen carbonate, potassium carbonate, potassium hydrogen carbonate, guanidine carbonate, guanidine hydrogen carbonate, lithium carbonate, calcium carbonate, magnesium carbonate, barium carbonate, ammonium carbonate, ammonium hydrogen carbonate and mixtures thereof. Percarbonate salts may also be utilized to provide both the source of carbonate ions and oxidizing agent. Preferred sources of carbonate ions, carbamate and hydrocarbonate ions are sodium hydrogen carbonate, potassium hydrogen carbonate, ammonium carbamate, and mixtures thereof.

According to the present invention the compositions comprise from about 0.1% to about 15% by weight, preferably from about 1% to about 10% by weight, and most preferably from about 1% to about 8% by weight of a hydrogencarbonate ion and from about 0.1% to about 10% by weight, preferably from about 1% to about 7% by weight, and most preferably from about 2% to about 5% by weight of a source of hydrogen peroxide.

Especially preferred oxidants for developing the hair color are mainly hydrogen peroxide or a compound of addition of hydrogen peroxide to urea, melamine, sodium borate or sodium carbonate, in the form of about 3% to about 12%, preferably about 6%, aqueous solution, as well as air oxygen. When about 6% hydrogen peroxide solution is used as the oxidant, the weight ratio of hair colorant to oxidant is 5:1 to 2:1, and preferably 1:1. Larger amounts of oxidant are used primarily when the hair colorant contains a higher dye concentration or when stronger hair bleaching is desired at the same time.

To use the afore-described colorants for oxidative dyeing of hair, said colorants are mixed with an oxidant immediately before use, and the mixture is applied to hair in an amount sufficient for hair.

The colorant according to the invention is generally used by applying an amount of the hair colorant sufficient for the hair coloring, about 30 grams to about 200 grams depending on hair length, to the hair, allowing the hair colorant to act at about 15° C. to about 50° C. for about 1 minute to about 60 minutes, preferably about 5 minutes to about 30 minutes, then rinsing the hair thoroughly with water, optionally washing with a shampoo and/or after-treating with a hair-conditioning composition, and finally drying.

In addition, if no oxidizing agents are added to the coloring mass, the above-described colorant can comprise natural or synthetic polymers or modified polymers of natural origin customary for cosmetic compositions, as a result of which setting of the hair is achieved at the same time as the coloring. Such compositions are generally referred to as color setting compositions.

The abovementioned polymers may be present in the colorant (a) according to the invention in the amounts customary for such agents, in particular in an amount of from about 1% to about 5% by weight. The pH of the color setting composition or color setting composition according to the invention is preferably about 4 to about 10.

The hair colorant with additional setting properties is used in a known and customary manner by wetting the hair with the setting composition, arranging (styling) the hair into the hairstyle and then drying.

The colorant according to the invention permits a coloration of keratin fibers, in particular of human hair, with a very strong color intensity and brilliance, and a very good durability (washing fastness), specially when applied together with hydrogen peroxide to natural hair or damaged hair (e.g., bleached or permed hair).

The zwitterionic azomethine dyes according to the invention of the general formula (I), (II), or (III) can be prepared via a 2-step process, by condensation of aromatic or heteroaromatic hydrazine or the acid addition salt thereof (commercially available or accessible via standard literature procedure) with heterocyclic aldehydes or ketones. The resulting azomethine dye is converted to the zwitterionic azomethine dye of the formula (I), (II), or (III) using sultones, such as, for example, butane sultone or propane sultone according to the reaction below:

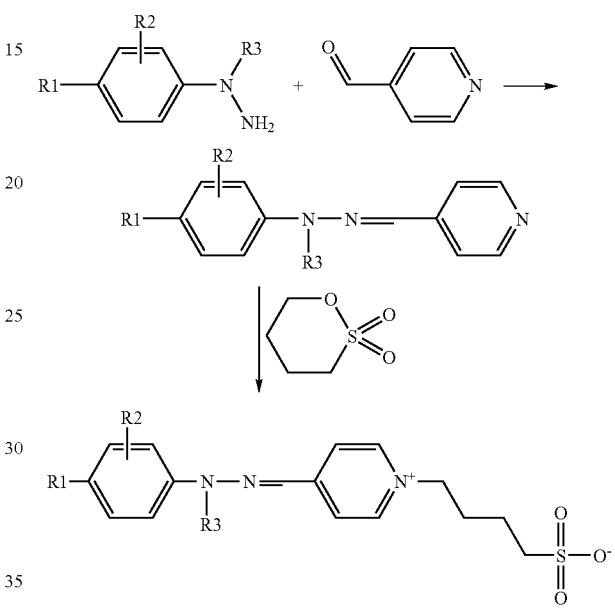

Another preparation process is a one-step process, by the condensation of an aromatic or heteroaromatic hydrazine with a previously prepared zwitterionic aldehyde or ketone according to the reaction below:

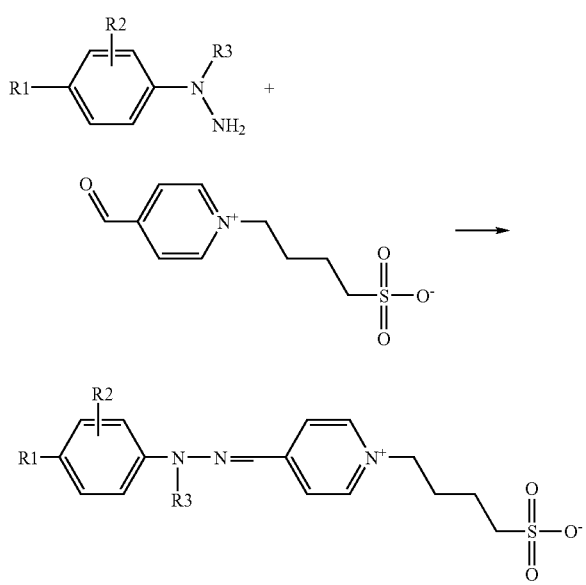

The examples below are intended to illustrate the subject-matter of the invention in more detail without limiting it thereto.

EXAMPLES

Example 1

Synthesis of azomethine butanesulfonates of formula (I)

Example 1a

Synthesis of 4-(4-{[methyl(phenyl)hydrazono]methyl}-1-pyridiniumyl)-1-butanesulfonate 4.5 g isonicotinaldehyde methyl(phenyl)hydrazone is heated under stirring with 50 ml butane sultone at 110° C. for 2 hours. After cooling, the resulting precipitate is filtered off and washed with acetone. The cake was triturated in acetone, filtered off, and dried.

6.9 g 4-(4-{[methyl(phenyl)hydrazono]methyl}-1-pyridiniumyl)-1-butanesulfonate is obtained as a bright yellow powder.

$^1$H-NMR (300 MHz, DMSO): δ=8.83 (d, J=6.3, 2H, H(2) and H(6) pyridinium); 8.16 (d, J=6.3, 2H, H(3) and H(5)-pyridinium); 7.80 (s, 1H, azomethine); 7.60 (d, J=7.8, 2H, H(2) and H(6)-phenyl); 7.41 (m, 2H, H(3) and H(5)-phenyl); 7.12 (m, 1H, H(4)-phenyl); 4.50 (t, J=7.5, 2H, N$^+$CH2); 3.59 (s, 3H, N—CH3); 2.48 (t, J=7.5, 2H, CH2-SO3$^-$); 1.99 (quintett, J=7.5, 2H, CH2); 1.58 (quintett, J=7.5, 2H, CH2).

API-ES MS: 370 [M$^+$+Na] (100)

Example 1b

Synthesis of 4-(3-{[methyl(phenyl)hydrazono]methyl}-1-pyridiniumyl)-1-butanesulfonate Analogously to the process described in example 1a, 4-(3-{[methyl(phenyl)hydrazono]-methyl}-1-pyridiniumyl)-1-butanesulfonate is prepared from 3-{[methyl(phenyl)-hydrazono]methyl}pyridine.

$^1$H-NMR (300 MHz, DMSO): δ=9.28 (s, 1H, H(2)-pyridinium); 8.90 (d, J=6.3, 1H, H(6)-pyridinium); 8.74 (d, J=7.8, 1H, H(4)-pyridinium); 8.10 (dd, J=6.3, J=7.8, 1H, H(5)-pyridinium); 7.75 (s, 1H, azomethine); 7.56 (d, J=8.7, 2H, H(2) and H(6)-phenyl); 7.37 (m, 2H, H(3) and H(5)-phenyl); 7.02 (m, 1H, H(4)-phenyl); 4.67 (t, J=7.5, 2H, N$^+$CH2); 3.51 (s, 3H, N—CH3); 2.48 (t, J=7.5, 2H, CH2-SO3$^-$); 2.09 (quintett, J=7.5, 2H, CH2); 1.61 (quintett, J=7.5, 2H, CH2).

API-ES MS: 370 [M$^+$+Na] (100)

Example 1c

Synthesis of 4-(2-{[methyl(phenyl)hydrazono]methyl}-1-pyridiniumyl)-1-butanesulfonate Analogously to the process described in example 1a, 4-(2-{[methyl(phenyl)hydrazono]-methyl}-1-pyridiniumyl)-1-butanesulfonate is prepared from 2-{[methyl(phenyl)-hydrazono]methyl}pyridine.

$^1$H-NMR (300 MHz, DMSO): δ=8.81 (d, J=6.3, 1H, H(6)-pyridinium); 8.57 (d, J=8.7, 1H, H(3)-pyridinium); 8.35 (m, 1H, H(4)-pyridinium); 7.85 (s, 1H, azomethine); 7.80 (dd, J=6.3, J=7.5, 1H, H(5)-pyridinium); 7.61 (d, J=8.4, 2H, H(2) and H(6)-phenyl); 7.43 (m, 2H, H(3) and H(5)-phenyl); 7.15 (m, 1H, H(4)-phenyl); 4.78 (t, J=7.5, 2H, N$^+$CH2); 3.72 (s, 3H, N—CH3); 2.54 (t, J=7.5, 2H, CH2-SO3$^-$); 2.05 (quintett, J=7.5, 2H, CH2); 1.75 (quintett, J=7.5, 2H, CH2).

API-ES MS: 370 [M$^+$+Na] (100)

Example 1d

Synthesis of 4-[4-{[4-(methoxy)phenyl]hydrazono}methyl)-1-pyridiniumyl]-1-butanesulfonate Analogously to the process described in example 1a, 4-[4-({[4-(methoxy)phenyl]-hydrazono}methyl)-1-pyridiniumyl]-1-butanesulfonate is prepared from isonicotinaldehyde (4-methoxyphenyl)hydrazone.

$^1$H-NMR (300 MHz, DMSO): δ=8.76 (d, J=6.3, 2H, H(2) and H(6) pyridinium); 8.11 (d, J=6.3, 2H, H(3) and H(5)-pyridinium); 7.82 (s, 1H, azomethine); 7.60 (d, J=7.8, 2H, H(2) and H(6)-phenyl); 6.95 (d, J=8.7, 2H, H(3) and H(5)-phenyl); 4.46 (t, J=7.5, 2H, N$^+$CH2); 3.74 (s, 3H, OCH3); 2.46 (t, J=7.5, 2H, CH2-SO3$^-$); 1.99 (quintett, J=7.5, 2H, CH2); 1.58 (quintett, J=7.5, 2H, CH2).

API-ES MS: 386 [M$^+$+Na] (100)

Example 1e

Synthesis of 4-[4-({methyl[4-(methoxy)phenyl]hydrazono}methyl)-1-pyridiniumyl]-1-butanesulfonate To a solution of 0.5 g 4-[4-{[4-(methoxy)phenyl]hydrazono}methyl)-1-pyridiniumyl]-1-butanesulfonate (example 1d) in 10 ml N-methylpyrrolidine is added 0.77 g potassium hydroxide and 1.96 g methyliodide. The reaction mixture is stirred overnight at room temperature. 200 ml acetone is added to the reaction mixture and the resulting precipitate is filtered off, washed with ethylacetate, and dried under vacuum. 0.36 g 4-[4-({methyl[4-(methoxy)phenyl]hydrazono}methyl)-1-pyridiniumyl]-1-butanesulfonate is obtained as an orange powder.

$^1$H-NMR (300 MHz, DMSO): δ=8.78 (d, J=6.3, 2H, H(2) and H(6)-pyridinium); 8.09 (d, J=6.3, 2H, H(3) and H(5)-pyridinium); 7.69 (s, 1H, azomethine); 7.51 (d, J=9.0, 2H, H(2) and H(6)-phenyl); 6.98 (d, J=9.0, 2H, H(3) and H(5)-phenyl); 4.47 (t, J=7.2, 2H, N$^+$CH2); 3.77 (s, 3H, OCH3); 3.57 (s, 3H, NCH3); 2.51 (t, J=7.5, 2H, CH2-SO3$^-$); 1.98 (quintett, J=7.5, 2H, CH2); 1.58 (quintett, J=7.5, 2H, CH2).

API-ES MS: 400 [M$^+$+Na] (100)

Example 1f

Synthesis of 4-(2-{[methyl(phenyl)hydrazono]methyl}-1,3-thiazol-3-ium-3-yl)-1-butanesulfonate Analogously to the process described in example 1a, 4-(2-{[methyl(phenyl)-hydrazono]methyl}-1,3-thiazol-3-ium-3-yl)-1-butanesulfonate is prepared from 2-{[methyl(phenyl)hydrazono]methyl}-1,3-thiazole.

$^1$H-NMR (300 MHz, DMSO): δ=8.28 (d, J=3.9, 1H, H(4)-thiazolium); 8.11 (s, 1H, azomethine); 8.00 (d, J=3.9, 1H, H(5)-thiazolium); 7.54-7.43 (m, 4H, H-phenyl); 7.20 (m, 1H, H(4)-phenyl); 4.60 (t, J=7.5, 2H, N$^+$CH2); 3.70 (s, 3H, N—CH3); 2.53 (t, J=7.5, 2H, CH2-SO3⁻); 1.97 (quintett, J=7.5, 2H, CH2); 1.68 (quintett, J=7.5, 2H, CH2).
API-ES MS: 376 [M⁺+Na] (100)

Example 2

Synthesis of azomethine butanesulfonates of formula (II)

Example 2a

Synthesis of 4-(4-{[2-(3-methyl-1,3-benzothiazol-2 (3H)-ylidene)hydrazono]methyl}-1-pyridiniumyl)-1-butanesulfonate 0.3 g isonicotinaldehyde-3-methyl-1,3-benzothiazol-2 (3H)-ylidene)-hydrazone is dissolved in 10 ml of dry 3-methoxypropanenitrile and heated under stirring to 100° C. Then 150 mg butane sultone is added dropwise while the mixture turns orange. Then the oil bath temperature is raised to 150° C. and stirring is continued. After 4 hours the reaction mixture is allowed to cool to 0° C. in an ice bath and the resulting precipitate is filtered off, washed with cold acetone, and dried under vacuum.

0.32 g 4-(4-{[2-(3-methyl-1,3-benzothiazol-2(3H)-ylidene)hydrazono]methyl}-1-pyridiniumyl)-1-butanesulfonate is obtained as an orange powder.

$^1$H-NMR (DMSO/300 MHz): δ=9.00 (d, 2H, J=6.3, pyridinium); 8.51 (s, 1H, azomethine); 8.25 (d, 2H, J=6.3, pyridinium); 7.76 (d, 1H, benzothiazole); 7.44-7.49 (m, 2H, benzothiazole); 7.24 (t, 1H, benzothiazole); 4.57 (t, 2H, CH$_2$); 3.71 (s, 3H, CH$_3$); 2.46 (t, 2H, CH$_2$); 2.02 (quintett, 2H, CH$_2$); 1,61 (quintett, 2H, CH$_2$).

Example 2b

Synthesis of 4-(3-{[2-(3-methyl-1,3-benzothiazol-2 (3H)-ylidene)hydrazono]methyl}-1-pyridiniumyl)-1-butanesulfonate Analogously to the process described in example 2a, 4-(3-{[2-(3-methyl-1,3-benzothiazol-2(3H)-ylidene)hydrazono]methyl}-1-pyridiniumyl)-1-butanesulfonate is prepared from nicotinaldehyde-(3-methyl-1,3-benzothiazol-2(3H)-ylidene)hydrazone.

$^1$H-NMR (DMSO/300 MHz): δ=9.32 (s, 1H, pyridinium); 9.05 (d, 1H, pyridinium); 8.79 (d, 1H, pyridinium); 8.49 (s, 1H, azomethine); 8.18 (t, 1H, pyridinium); 7.70 (d, 1H, benzothiazole); 7.42-7.40 (m, 2H, benzothiazole); 7.21-7.16 (m, 1H, benzothiazole); 4.68 (t, 2H, CH$_2$); 3.65 (s, 3H, CH$_3$); 2.50 (t, 2H, CH$_2$); 2.07 (quintett, 2H, CH$_2$); 1.63 (quintett, 2H, CH$_2$).

Example 2c

Synthesis of 4-(4-{[2-(3,4-dimethyl-1,3-thiazol-2 (3H)-ylidene)hydrazono]methyl}-1-pyridiniumyl)-1-butanesulfonate Analogously to the process described in example 2a, 4-(4-{[2-(3,4-dimethyl-1,3-thiazol-2(3H)-ylidene)hydrazono] methyl}-1-pyridiniumyl)-1-butanesulfonate is prepared (3,4-dimethyl-1,3-thiazol-2(3H)-ylidene)hydrazone.

$^1$H-NMR (DMSO/300 MHz): δ=8.87 (d, 2H, J=6.3, pyridinium); 8.30 (s, 1H, azomethine); 8.13 (d, 2H, J=6.3, pyridinium); 6.46 (s, 1H, thiazole); 4.51 (t, 2H, CH$_2$); 3.43 (s, 3H, CH$_3$); 2.56-2.45 (m, 5H, CH$_2$, CH$_3$, overlap); 1.96 (m, 2H, CH$_2$); 1.58 (m, 2H, CH$_2$).

Example 3 to 11

Hair Colorant

| | |
|---|---|
| 2.5 mmol | Dye of the formula (I), (II), or (III) |
| 5.0 g | Ethanol |
| 4.0 g | Decyl glucoside |
| 0.2 g | Ethylenediaminotetraacetic acid disodium salt |
| Balance to 100.0 g | Water, demineralized |

If necessary, the coloring solution is adjusted to the pH values given in table 1 by adding 25% ammonia.

The hair coloring is carried out by applying an amount of the colorant sufficient for the hair coloring to the hair and distributing it evenly using a brush. After a contact time of 30 minutes at 40° C., the hair is rinsed with lukewarm water, washed with a shampoo, rinsed with lukewarm water, and then dried.

The coloring results are summarized in table 1 below.

TABLE 1

| Ex. | Compound of the formula (I), (II), or (III) (as in examples 1 to 2) | pH of the colorant | Color shade after coloring | Color measurement values after coloring |
|---|---|---|---|---|
| — | Color shade of the hair before the coloring treatment | — | — | L = 80.60<br>C = 12.10<br>h = 92.10 |
| 3 | 4-(4-{[methyl(phenyl)hydrazono]-methyl}-1-pyridiniumyl)-1-butanesulfonate (1a) | 7.3 | bright golden yellow | L = 78.16<br>C = 91.84<br>h = 92.70 |
| 4 | 4-(3-{[methyl(phenyl)hydrazono]-methyl}-1-pyridiniumyl)-1-butanesulfonate (1b) | 7.7 | Bright lemon yellow | L = 80.21<br>C = 67.67<br>h = 98.10 |
| 5 | 4-(2-{[methyl(phenyl)hydrazono]-methyl}-1-pyridiniumyl)-1-butanesulfonate (1c) | 7.4 | Bright lemon yellow | L = 80.41<br>C = 72.35<br>h = 99.20 |
| 6 | 4-[4-({[4-(methoxy)phenyl]-hydrazono}methyl)-1-pyridiniumyl]-1-butanesulfonate (1d) | 6.0 | Bright orange | L = 64.39<br>C = 77.09<br>h = 67.10 |

TABLE 1-continued

| Ex. | Compound of the formula (I), (II), or (III) (as in examples 1 to 2) | pH of the colorant | Color shade after coloring | Color measurement values after coloring |
|---|---|---|---|---|
| 7 | 4-[4-({methyl[4-(methoxy)phenyl]-hydrazono}methyl)-1-pyridiniumyl]-1-butanesulfonate (1e) | 7.3 | Bright orange-yellow | L = 61.40<br>C = 74.69<br>h = 72.50 |
| 8 | 4-(2-{[methyl(phenyl)hydrazono]-methyl}-1,3-thiazol-3-ium-3-yl)-1-butanesulfonate (1f) | 6.0 | Bright lemon yellow | L = 81.13<br>C = 81.32<br>h = 97.20 |
| 9 | 4-(4-{[2-(3-methyl-1,3-benzothiazol-2(3H)-ylidene)hydrazono]methyl}-1-pyridiniumyl)-1-butanesulfonate (2a) | 7.3 | orange | L = 73.90<br>C = 56.22<br>h = 80.00 |
| 10 | 4-(3-{[2-(3-methyl-1,3-benzothiazol-2(3H)-ylidene)hydrazono]methyl}-1-pyridiniumyl)-1-butanesulfonate (2b) | 7.2 | lemon yellow | L = 78.49<br>C = 51.92<br>h = 95.90 |
| 11 | 4-(4-{[2-(3,4-dimethyl-1,3-thiazol-2(3H)-ylidene)hydrazono]methyl}-1-pyridiniumyl)-1-butanesulfonate (2d) | 6.8 | red | L = 43.66<br>C = 62.88<br>h = 37.80 |

Example 12

Hair Colorant with Cationic Surface-active Substances

| 0.87 g | 4-(4-{[methyl(phenyl)hydrazono]methyl}-1-pyridiniumyl)-1-butanesulfonate (1a) |
| 5.00 g | Ethanol |
| 4.00 g | Cetyltrimethylammonium chloride, 25% in water |
| Balance to 100.00 g | Water, demineralized |

The pH is adjusted to the pH values given in table 2 using 25% ammonia.

The hair coloring was carried out by applying an amount of the colorant sufficient for the hair coloring to the hair and distributing it evenly using a brush. After a contact time of 30 minutes at 40° C., the hair is rinsed with lukewarm water, washed with a shampoo, rinsed again with lukewarm water, and then dried.

The coloring results are summarized in table 2 below.

TABLE 2

| Ex. | Compound of the formula (I) | pH of the colorant | Color shade after coloring | Color measurement values after coloring |
|---|---|---|---|---|
| — | Color shade of the hair before the coloring treatment | — | — | L = 80.60<br>C = 12.10<br>h = 92.10 |
| 12 | 4-(4-{[methyl(phenyl)hydrazono]-methyl}-1-pyridiniumyl)-1-butanesulfonate (1a) | 9.3 | Bright golden yellow | L = 78.95<br>C = 92.05<br>h = 93.60 |

Example 13

Hair Colorant with Amphoteric Surface-active Substances

| 0.87 g | 4-(4-{[methyl(phenyl)hydrazono]methyl}-1-pyridiniumyl)-1-butanesulfonate (1a) |
| 5.00 g | Ethanol |
| 7.50 g | Coconut fatty acid amidopropylbetaine |
| Balance to 100.00 g | Water, demineralized |

The pH is adjusted to the pH values given in table 3 using 25% ammonia. The hair coloring is carried out by applying an amount of the colorant sufficient for the hair coloring to the hair and distributing it evenly using a brush. After a contact time of 30 minutes at 40° C., the hair is rinsed with lukewarm water, washed with a shampoo, rinsed again with lukewarm water, and then dried.

The coloring results are summarized in table 3 below.

TABLE 3

| Ex. | Compound of the formula (I) | pH of the colorant | Color shade after coloring | Color measurement values after coloring |
|---|---|---|---|---|
| — | Color shade of the hair before the coloring treatment | — | — | L = 80.60<br>C = 12.10<br>h = 92.10 |
| 13 | 4-(4-{[methyl(phenyl)hydrazono]-methyl}-1-pyridiniumyl)-1-butanesulfonate (1a) | 9.7 | Bright golden yellow | L = 76.65<br>C = 90.42<br>h = 93.20 |

Example 14

Hair Colorant with Anionic Surface-active Substances

| 0.87 g | 4-(4-{[methyl(phenyl)hydrazono]methyl}-1-pyridiniumyl)-1-butanesulfonate (1a) |
| 5.00 g | Ethanol |

-continued

| | |
|---|---|
| 7.50 g | Lauryl ether sulfate, 28% in water |
| Balance to 100.00 g | Water, demineralized |

The pH is adjusted to the pH values given in table 4 using 25% ammonia.

The hair coloring is carried out by applying an amount of the colorant sufficient for the hair coloring to the hair and distributing it evenly using a brush. After a contact time of 30 minutes at 40° C., the hair is rinsed with lukewarm water, washed with a shampoo, rinsed again with lukewarm water, and then dried.

The coloring results are summarized in table 4 below.

TABLE 4

| Ex. | Compound of the formula (I) | pH of the colorant | Color shade after coloring | Color measurement values after coloring |
|---|---|---|---|---|
| — | Color shade of the hair before the coloring treatment | — | — | L = 80.60<br>C = 12.10<br>h = 92.10 |
| 14 | 4-(4-{[methyl(phenyl)hydrazono]-methyl}-1-pyridiniumyl)-1-butanesulfonate (1a) | 9.1 | Bright lemon yellow | L = 80.67<br>C = 79.86<br>h = 96.70 |

Examples 15 to 23

Hair Colorant with Oxidizing Agent

| | |
|---|---|
| 0.6 g | Dye of the formula (I), (II), or (III) as in table 5 |
| 5.0 g | Ethanol |
| 4.0 g | Decyl glucoside |
| 0.2 g | Ethylenediaminotetraacetic acid disodium salt |
| Balance to 100.0 g | Water, demineralized |

5 g of the above color carrier mass is mixed with 5 g of a 9% strength hydrogen peroxide solution. The pH is adjusted to 9.5 using 25% strength ammonia.

The resulting ready-to-use hair colorant is applied to the hair and distributed evenly using a brush. After a contact time of 30 minutes at 40° C., the hair is rinsed with lukewarm water, washed with a shampoo, rinsed again with lukewarm water, and then dried.

The coloring results are summarized in table 5 below.

TABLE 5

| Ex. | Compound of the formula (I), (II), or (III) (as in examples 1 to 2) | Color shade after coloring | Color mesurement values after coloring |
|---|---|---|---|
| — | Color shade of the hair before the coloring treatment | — | L = 80.60<br>C = 12.10<br>h = 92.10 |
| 15 | 4-(4-{[methyl(phenyl)hydrazono]-methyl}-1-pyridiniumyl)-1-butanesulfonate (1a) | bright golden yellow | L = 80.52<br>C = 88.40<br>h = 94.40 |
| 16 | 4-(3-{[methyl(phenyl)hydrazono]-methyl}-1-pyridiniumyl)-1-butanesulfonate (1b) | Bright lemon yellow | L = 82.38<br>C = 52.23<br>h = 99.70 |
| 17 | 4-(2-{[methyl(phenyl)hydrazono]-methyl}-1-pyridiniumyl)-1-butanesulfonate (1c) | Bright lemon yellow | L = 82.75<br>C = 72.56<br>h = 98.80 |
| 18 | 4-[4-({[4-(methoxy)phenyl]-hydrazono}methyl)-1-pyridiniumyl]-1-butanesulfonate (1d) | Bright orange | L = 64.13<br>C = 80.12<br>h = 65.00 |
| 19 | 4-[4-({methyl[4-(methoxy)-phenyl]hydrazono}methyl)-1-pyridiniumyl]-1-butanesulfonate (1e) | Bright orange-yellow | L = 68.19<br>C = 81.42<br>h = 76.30 |
| 20 | 4-(2-{[methyl(phenyl)hydrazono]-methyl}-1,3-thiazol-3-ium-3-yl)-1-butanesulfonate (1f) | Bright lemon yellow | L = 82.24<br>C = 75.95<br>h = 97.90 |
| 21 | 4-(4-{[2-(3-methyl-1,3-benzothiazol-2(3H)-ylidene)-hydrazono]methyl}-1-pyridiniumyl)-1-butanesulfonate (2a) | orange | L = 73.29<br>C = 68.90<br>h = 76.30 |
| 22 | 4-(3-{[2-(3-methyl-1,3-benzothiazol-2(3H)-ylidene)-hydrazono]methyl}-1-pyridiniumyl)-1-butanesulfonate (2b) | Lemon yellow | L = 81.29<br>C = 63.29<br>h = 96.9 |
| 23 | 4-(4-{[2-(3,4-dimethyl-1,3-thiazol-2(3H)-ylidene)hydrazono]methyl}-1-pyridiniumyl)-1-butanesulfonate (2d) | red | L = 51.70<br>C = 59.96<br>h = 39.7 |

Examples 24 to 28

Hair Colorant with Oxidizing Agent

| | |
|---|---|
| 5.0 mmol | Dye of the formula (I), (II), or (III) as in table 6 |
| 5.0 g | Ethanol |
| 4.0 g | Decyl glucoside |
| 0.2 g | Ethylenediaminotetraacetic acid disodium salt |
| Balance to 100.0 g | Water, demineralized |

5 g of the above color carrier mass is mixed with 5 g of a 9% strength hydrogen peroxide solution. The pH is adjusted to 9.0 using 25% ammonia.

The resulting ready-to-use hair colorant is applied to natural hair and distributed evenly using a brush. After a contact time of 30 minutes at 40° C., the hair is rinsed with lukewarm water, washed with a shampoo, rinsed again with lukewarm water, and then dried. The washing process is repeated five times. The colors did not change visually.

TABLE 6

| Ex. | Compound of the formula (I), (II), or (III) (as in examples 1 to 2) | Color shade after coloring | Color shade after washing |
|---|---|---|---|
| — | Color shade of the hair before the coloring treatment | L = 32.07<br>C = 13.40<br>h = 65.10 | |
| 24 | 4-(4-{[methyl(phenyl)hydrazono]-methyl}-1-pyridiniumyl)-1-butanesulfonate (1a) | middle blond with yellow reflex<br>L = 37.06<br>C = 28.27<br>h = 78.80 | middle blond with yellow reflex<br>L = 37.22<br>C = 26.40<br>h = 77.80<br>ΔL = 0.16 |
| 25 | 4-(3-{[methyl(phenyl)hydrazono]-methyl}-1-pyridiniumyl)-1-butanesulfonate (1b) | middle blond with yellow reflex<br>L = 36.92 | middle blond with yellow reflex<br>L = 35.09<br>C = 20.40 |

TABLE 6-continued

| Ex. | Compound of the formula (I), (II), or (III) (as in examples 1 to 2) | Color shade after coloring | Color shade after washing |
|---|---|---|---|
| 26 | 4-(2-{[methyl(phenyl)hydrazono]-methyl}-1,3-thiazol-3-ium-3-yl)-1-butanesulfonate (1f) | C = 22.47<br>h = 76.70<br>middle blond with yellow reflex<br>L = 37.20<br>C = 24.43<br>h = 77.70 | h = 73.20<br>ΔL = 1.83<br>middle blond with yellow reflex<br>L = 36.54<br>C = 22.57<br>h = 75.40<br>ΔL = 0.66 |
| 27 | 4-(3-{[2-(3-methyl-1,3-benzothiazol-2(3H)-ylidene)-hydrazono]methyl}-1-pyridiniumyl)-1-butanesulfonate (2b) | middle blond with yellow reflex<br>L = 35.09<br>C = 18.79<br>h = 72.40 | middle blond with yellow reflex<br>L = 35.20<br>C = 18.28<br>h = 71.30<br>ΔL = 0.11 |

The L*C*h* color measurement values given in the present examples are ascertained using a calorimeter from Minolta, model Chromameter II. Here, the L value is the lightness (i.e., the lower the L value, the greater the color intensity), while the C value is a measure of the colorfulness ("chroma") (i.e., the greater the C value, the more colorful the color). The h value is the color shade angle ("hue").

Unless stated otherwise, all of the percentages given in the present application are percentages by weight.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An agent for the nonoxidative coloring of keratin fibers, comprising at least one zwitterionic azomethine dye of the general formula (I), (II), or (III)

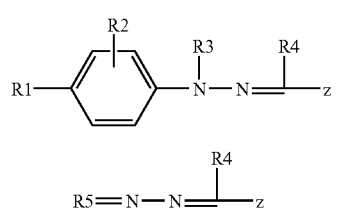

(I)

(II)

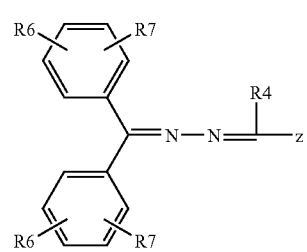

(III)

wherein

R1 and R2 may be identical or different and independently of one another, are selected from the group consisting of hydrogen, a halogen atom, a saturated or unsaturated $(C_1-C_{12})$-alkyl group, a $(C_1-C_{12})$-alkyl group substituted by a halogen atom, a hydroxyl group, a hydroxy-$(C_1-C_{12})$-alkyl group, a $(C_1-C_{12}$-alkoxy group, a cyano group, a nitro group, an amino group, a $(C_1-C_{12})$-alkylamino group, a $(C_1-C_{12})$-dialkylamino group, a carboxylic acid group, a C(O)O—$(C_1-C_{12})$-alkyl group, a substituted C(O)O-phenyl group, an unsubstituted C(O) O-phenyl group, a substituted phenyl group, an unsubstituted phenyl group, a substituted naphthyl group, an unsubstituted naphthyl group, a substituted heteroaryl group and an unsubstituted heteroaryl group;

R3 is selected from the group consisting of hydrogen, a saturated or unsaturated $(C_1-C_{12})$-alkyl group and a hydroxy-$(C_2-C_{12})$alkyl group, or forms with a carbon atom of the benzene ring a five or six-membered heterocycle which may be substituted with one or more $C_1-C_{12}$-alkyl groups;

R4 is selected from the group consisting of hydrogen, a saturated or unsaturated $(C_1-C_{12})$-alkyl group, a substituted phenyl group and an unsubstituted phenyl group;

R5 is selected from the group consisting of the general formula (XIV), (XV), and (XVI)

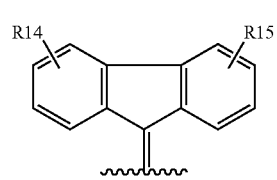

(XIV)

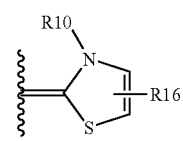

(XV)

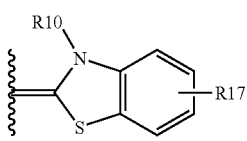

(XVI)

R6 and R7 may be identical or different and, independently of one another, are selected from the group consisting of hydrogen, a halogen atom, an amino group, a $(C_1-C_{12})$-alkylamino group, a $(C_1-C_{12})$-dialkylamino group, a $C_1$-$C_6$-alkylcyano group, a hydroxyl group, a nitro group, a saturated or unsaturated ($C_1$-$C_{12}$)-alkyl group, a hydroxy-($C_1$-$C_{12}$)-alkyl group, a ($C_1$-$C_{12}$)-alkoxy group, a methoxy-($C_1$-$C_{12}$)-alkyl group and a C(O)O—($C_1$-$C_{12}$)-alkyl group;

z is selected from the group consisting of heterocycles according to formula (IV) to (XII)

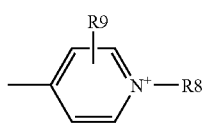
(IV)

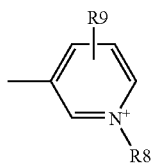
(V)

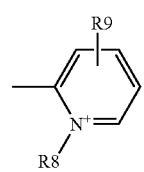
(VI)

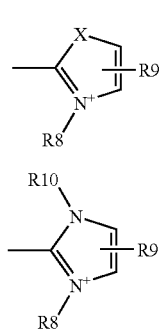
(VII)

(VIII)

(IX)

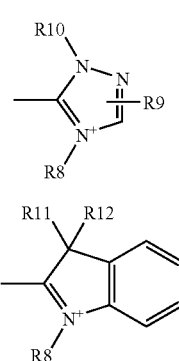
(X)

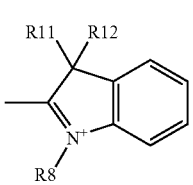

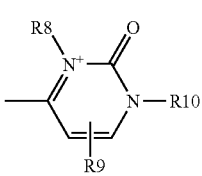
(XI)

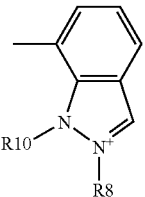
(XII)

X is oxygen or sulfur;
R8 is an alkyl sulfonate radical of the formula (XIII);

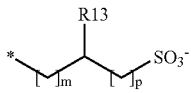
(XIII)

R9 is selected from the group consisting of hydrogen, a halogen atom, a saturated or unsaturated ($C_1$-$C_{12}$)-alkyl group, a ($C_1$-$C_{12}$)-alkyl group substituted by a halogen atom, a hydroxyl group, a hydroxy-($C_2$-$C_{12}$)-alkyl group, a ($C_1$-$C_{12}$)-alkoxy group, a cyano group, a nitro group, an amino group, a ($C_1$-$C_{12}$)-alkylamino group, a ($C_1$-$C_{12}$)-dialkylamino group, a carboxylic acid group, a C(O)O—($C_1$-$C_{12}$)-alkyl group, a substituted or unsubstituted C(O)O-phenyl group, a substituted or unsubstituted phenyl group, and a benzene ring condensed to the heteroaromatic ring of formula (IV) to (XII);

R10 is selected from the group consisting of a saturated or unsaturated ($C_1$-$C_{12}$)-alkyl group or a saturated or unsaturated hydroxy-($C_1$-$C_{12}$)-alkyl group;

R11 and R12 may be identical or different and independently of one another, are a saturated or unsaturated ($C_1$-$C_{12}$)-alkyl group;

R13 is hydrogen or a hydroxyl group;

R14, R15, R16, and R17 may be identical or different and independently of one another, are selected from the group consisting of hydrogen, a halogen atom, a saturated or unsaturated ($C_1$-$C_{12}$)-alkyl group, a ($C_1$-$C_{12}$)-alkyl group substituted by a halogen atom, a hydroxyl group, a hydroxy-($C_1$-$C_{12}$)-alkyl group, a ($C_1$-$C_{12}$)-alkoxy group, a cyano group, a nitro group, an amino group, a ($C_1$-$C_{12}$)-alkylamino group, a ($C_1$-$C_{12}$)-dialkylamino group, a carboxylic acid group, a C(O)O—($C_1$-$C_{12}$)-alkyl group, a substituted C(O)O-phenyl group, an unsubstituted C(O)O-phenyl group, a substituted phenyl group and an unsubstituted phenyl group, m is in a range of 0 to (n−1);
p is in a range of 0 to (n−1) with m+p=(n−1) and
n is an integer from 1 to 6; and further comprising at least one polymer which is selected from the group consisting of natural polymers customary for cosmetic agents, synthetic polymers and modified polymers of natural origin, and being in the form of a color setting composition.

2. An agent for the simultaneous lightening and coloring of keratin fibers, comprising at least one zwitterionic azomethine dye of the general formula (I), (II), or (III)

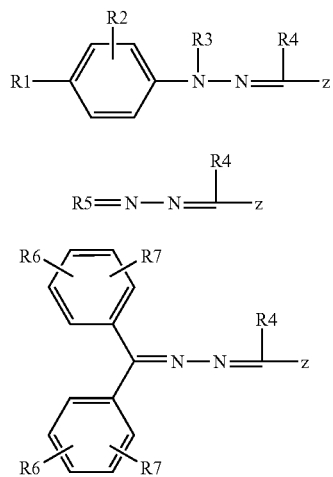
(I)

(II)

(III)

wherein
- R1 and R2 may be identical or different and independently of one another, are selected from the group consisting of hydrogen, a halogen atom, a saturated or unsaturated $(C_1\text{-}C_{12})$-alkyl group, a $(C_1\text{-}C_{12})$-alkyl group substituted by a halogen atom, a hydroxyl group, a hydroxy-$(C_1\text{-}C_{12})$-alkyl group, a $(C_1\text{-}C_{12})$-alkoxy group, a cyano group, a nitro group, an amino group, a $(C_1\text{-}C_{12})$-alkylamino group, a $(C_1\text{-}C_{12})$-dialkylamino group, a carboxylic acid group, a C(O)O—$(C_1\text{-}C_{12})$-alkyl group, a substituted C(O)O-phenyl group, an unsubstituted C(O)O-phenyl group, a substituted phenyl group, an unsubstituted phenyl group, a substituted naphthyl group, an unsubstituted naphthyl group, a substituted heteroaryl group and an unsubstituted heteroaryl group;
- R3 is selected from the group consisting of hydrogen, a saturated or unsaturated $(C_1\text{-}C_{12})$-alkyl group, and a hydroxy-$(C_2\text{-}C_{12})$alkyl group, or forms with a carbon atom of the benzene ring a five or six-membered heterocycle which may be substituted with one or more $(C_1\text{-}C_{12})$-alkyl group;
- R4 is selected from the group consisting of hydrogen, a saturated or unsaturated $(C_1\text{-}C_{12})$-alkyl group, a substituted phenyl group and an unsubstituted phenyl group;
- R5 is selected from the group consisting of the general formula (XIV), (XV), and (XVI)

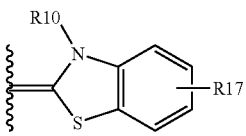
(XIV)

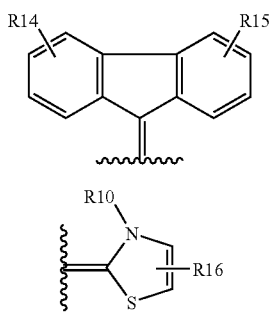
(XV)

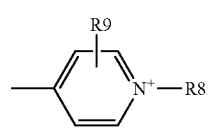
(XVI)

R6 and R7 may be identical or different and, independently of one another, are selected from the group consisting of hydrogen, a halogen atom, an amino group, a alkylamino group, a $(C_1\text{-}C_{12})$-dialkylamino group, a $C_1\text{-}C_6$-alkylcyano group, a hydroxyl group, a nitro group, a saturated or unsaturated $(C_1\text{-}C_{12})$-alkyl group, a hydroxy-$(C_1\text{-}C_{12})$-alkyl group, a $(C_1\text{-}C_{12})$-alkoxy group, a methoxy-$(C_1\text{-}C_{12})$-alkyl group and a C(O)O—$(C_1\text{-}C_{12})$-alkyl group;

z is selected from the group consisting of heterocycles of the formula (IV) to (XII)

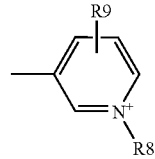
(IV)

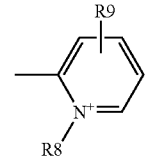
(V)

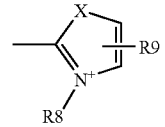
(VI)

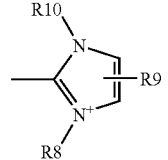
(VII)

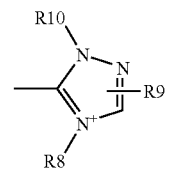
(VIII)

(IX)

-continued

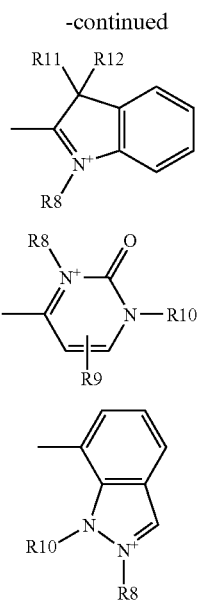

X is oxygen or sulfur;
R8 is an alkyl sulfonate radical of the formula (XIII);

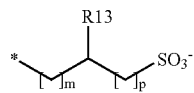

R9 is selected from the group consisting of hydrogen, a halogen atom, a saturated or unsaturated ($C_1$-$C_{12}$)-alkyl group, a ($C_1$-$C_{12}$)-alkyl group substituted by a halogen atom, a hydroxyl group, a hydroxy-($C_2$-$C_{12}$)-alkyl group, a ($C_1$-$C_{12}$)-alkoxy group, a cyano group, a nitro group, an amino group, a ($C_1$-$C_{12}$)-alkylamino group, a ($C_1$-$C_{12}$-dialkylamino group, a carboxylic acid group, a C(O)O—($C_1$-$C_{12}$)-alkyl group, a substituted or unsubstituted C(O)O-phenyl group, a substituted or unsubstituted phenyl group, and a benzene ring condensed to the heteroaromatic ring of formula (IV) to (XII);
R10 is selected from the group consisting of a saturated or unsaturated ($C_1$-$C_{12}$)-alkyl group and a saturated or unsaturated hydroxy-($C_1$-$C_{12}$)-alkyl group;
R11 and R12 may be identical or different and independently of one another, are a saturated or unsaturated ($C_1$-$C_{12}$)-alkyl group;
R13 is hydrogen or a hydroxyl group;
R14, R15, R16, and R17 may be identical or different and independently of one another, are selected from the group consisting of hydrogen, a halogen atom, a saturated or unsaturated ($C_1$-$C_{12}$)-alkyl group, a ($C_1$-$C_{12}$)-alkyl group substituted by a halogen atom, a hydroxyl group, a hydroxy-($C_1$-$C_{12}$)-alkyl group, a ($C_1$-$C_{12}$)-alkoxy group, a cyano group, a nitro group, an amino group, a ($C_1$-$C_{12}$)-alkylamino group, a ($C_1$-$C_{12}$)-dialkylamino group, a carboxylic acid group, a C(O)O—($C_1$-$C_{12}$)-alkyl group, a substituted C(O)O-phenyl group, an unsubstituted C(O)O-phenyl group, a substituted phenyl group and an unsubstituted phenyl group,
m is in a range of 0 to (n−1);
p is in a range of 0 to (n−1) with m+p=(n−1) and
n is an integer from 1 to 6; and further comprising an oxidizing agent, wherein the oxidizing agent is selected from the group consisting of hydrogen peroxide and its addition compounds urea, melamine, sodium borate or sodium carbonate.

3. An oxidative colorant for coloring fibers based on at least one oxidation dye precursor, comprising at least one zwitterionic azomethine dye of the general formula (I), (II), or (III)

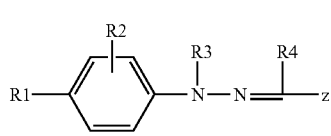

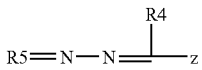

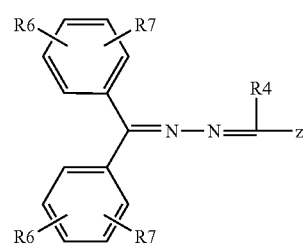

wherein
R1 and R2 may be identical or different and independently of one another, are selected from the group consisting of hydrogen, a halogen atom, a saturated or unsaturated ($C_1$-$C_{12}$)-alkyl group, a ($C_1$-$C_{12}$)-alkyl group substituted by a halogen atom, a hydroxyl group, a hydroxy-($C_1$-$C_{12}$)-alkyl group, a ($C_1$-$C_{12}$)-alkoxy group, a cyano group, a nitro group, an amino group, a ($C_1$-$C_{12}$)-alkylamino group, a ($C_1$-$C_{12}$)-dialkylamino group, a carboxylic acid group, a C(O)O—($C_1$-$C_{12}$)-alkyl group, a substituted C(O)O-phenyl group, an unsubstituted C(O) O-phenyl group, a substituted phenyl group, an unsubstituted phenyl group, a substituted naphthyl group, an unsubstituted naphthyl group, a substituted heteroaryl group and an unsubstituted heteroaryl group;
R3 is selected from the group consisting of hydrogen, a saturated or unsaturated ($C_1$-$C_{12}$)-alkyl group and a hydroxy-($C_2$-$C_{12}$)alkyl group, or forms with a carbon atom of the benzene ring a five or six-membered heterocycle which may be substituted with one or more ($C_1$-$C_{12}$)-alkyl group;
R4 is selected from the group consisting of hydrogen, a saturated or unsaturated ($C_1$-$C_{12}$)-alkyl group, a substituted phenyl group and an unsubstituted phenyl group;
R5 is selected from the group consisting of the general formula (XIV), (XV) and (XVI)

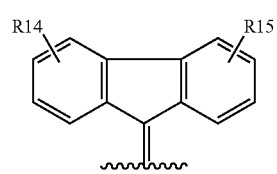

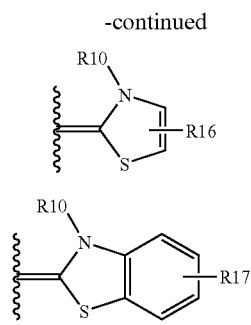 (XV)

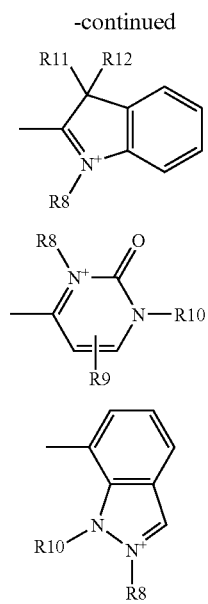

(X)

(XI)

(XII)

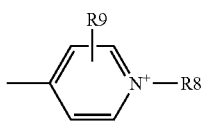 (XVI)

R6 and R7 may be identical or different and, independently of one another, are selected from the group consisting of hydrogen, a halogen atom, an amino group, a $(C_1-C_{12})$-alkylamino group, a $(C_1-C_{12})$-dialkylamino group, a $C_1-C_6$-alkylcyano group, a hydroxyl group, a nitro group, a saturated or unsaturated $(C_1-C_{12})$-alkyl group, a hydroxy-$(C_1-C_{12})$-alkyl group, a $(C_1-C_{12})$-alkoxy group, a methoxy-$(C_1-C_{12})$-alkyl group, and a C(O)O—$(C_1-C_{12})$-alkyl group;

z is selected from the group consisting of heterocycles of the formula (IV) to (XII)

X is oxygen or sulfur;
R8 is an alkyl sulfonate radical of the formula (XIII);

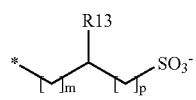 (XIII)

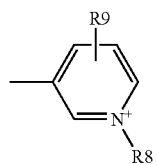 (IV)

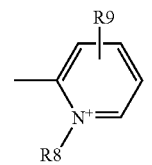 (V)

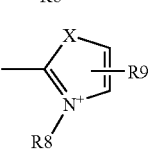 (VI)

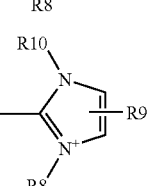 (VII)

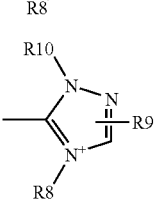 (VIII)

(IX)

R9 is selected from the group consisting of hydrogen, a halogen atom, a saturated or unsaturated $(C_1-C_{12})$-alkyl group, a $(C_1-C_{12})$-alkyl group substituted by a halogen atom, a hydroxyl group, a hydroxy-$(C_2-C_{12})$-alkyl group, a $(C_1-C_{12})$-alkoxy group, a cyano group, a nitro group, an amino group, a $(C_1-C_{12})$-alkylamino group, a ($C_1$-$C_{12}$-dialkylamino group, a carboxylic acid group, a C(O)O—$(C_1-C_{12})$-alkyl group, a substituted or unsubstituted C(O)O-phenyl group, a substituted or unsubstituted phenyl group, and a benzene ring condensed to the heteroaromatic ring of formula (IV) to (XII);

R10 is selected from the group consisting of a saturated or unsaturated $(C_1-C_{12})$-alkyl group and a saturated or unsaturated hydroxy-$(C_1-C_{12})$-alkyl group;

R11 and R12 may be identical or different and independently of one another, are a saturated or unsaturated $(C_1-C_{12})$-alkyl group;

R13 is hydrogen or a hydroxyl group;

R14, R15, R16, and R17 may be identical or different and independently of one another, are selected from the group consisting of hydrogen, a halogen atom, a saturated or unsaturated $(C_1-C_{12})$-alkyl group, a $(C_1-C_{12})$-alkyl group substituted by a halogen atom, a hydroxyl group, a hydroxy-$(C_1-C_{12})$-alkyl group, a $(C_1-C_{12})$-alkoxy group, a cyano group, a nitro group, an amino group, a $(C_1-C_{12})$-alkylamino group, a $(C_1-C_{12})$-dialkylamino group, a carboxylic acid group, a C(O)O—$(C_1-C_{12})$-alkyl group, a substituted C(O)O-phenyl group, an unsubstituted C(O)O-phenyl group, a substituted phenyl group and an unsubstituted phenyl group, m is in a range of 0 to (n−1);

p is in a range of 0 to (n−1) with m+p=(n−1) and n is an integer from 1 to 6; and further comprising an oxidizing agent, wherein the oxidizing agent is selected from the group consisting of hydrogen peroxide and its addition compounds to urea, melamine, sodium borate or sodium carbonate, and persulphates.

4. The agent according to claim 1, wherein in the formula (I), (II), and (III) R13 is hydrogen and n is 2 or 3.

5. The agent according to claim 1, wherein the zwitterionic azomethine dye of the formula (I), (II), or (III) is selected from the group consisting of 4-(4-{[methyl(phenyl)hydrazono]methyl}-1-pyridiniumyl)-1-butanesulfonate, 4-(3-{[methyl(phenyl)hydrazono]methyl}-1-pyridiniumyl)-1-butanesulfonate,
4-(2-{[methyl(phenyl)hydrazono]methyl}-1-pyridiniumyl)-1-butanesulfonate,
4-(4-{[(4-methoxyphenyl)(methyl)hydrazono]methyl}-1-pyridiniumyl)-1-butanesulfonate,
4-(3-{[(4-methoxyphenyl)(methyl)hydrazono]methyl}-1-pyridiniumyl)-1-butanesulfonate,
4-(2-{[(4-methoxyphenyl)(methyl)hydrazono]methyl}-1-pyridiniumyl)-1-butanesulfonate,
4-(4-{[(2-methoxyphenyl)(methyl)hydrazono]methyl}-1-pyridiniumyl)-1-butanesulfonate,
4-(3-{[(2-methoxyphenyl)(methyl)hydrazono]methyl}-1-pyridiniumyl)-1-butanesulfonate,
4-(2-{[(2-methoxyphenyl)(methyl)hydrazono]methyl}-1-pyridiniumyl)-1-butanesulfonate,
4-(4-{[(4-hydroxyphenyl)(methyl)hydrazono]methyl}-1-pyridiniumyl)-1-butanesulfonate,
4-(3-{[(4-hydroxyphenyl)(methyl)hydrazono]methyl}-1-pyridiniumyl)-1-butanesulfonate,
4-(2-{[(4-hydroxyphenyl)(methyl)hydrazono]methyl}-1-pyridiniumyl)-1-butanesulfonate,
4-(4-{[methyl(4-methylphenyl)hydrazono]methyl}-1-pyridiniumyl)-1-butanesulfonate,
4-(3-{[methyl(4-methylphenyl)hydrazono]methyl}-1-pyridiniumyl)-1-butanesulfonate,
4-(2-{[methyl(4-methylphenyl)hydrazono]methyl}-1-pyridiniumyl)-1-butanesulfonate,
4-(4-{[(4-chlorophenyl)(methyl)hydrazono]methyl}-1-pyridiniumyl)-1-butanesulfonate,
4-(3-{[(4-chlorophenyl)(methyl)hydrazono]methyl}-1-pyridiniumyl)-1-butanesulfonate,
4-(2-{[(4-chlorophenyl)(methyl)hydrazono]methyl}-1-pyridiniumyl)-1-butanesulfonate,
4-(4-{[methyl(4-nitrophenyl)hydrazono]methyl}-1-pyridiniumyl)-1-butanesulfonate,
4-(3-{[methyl(4-nitrophenyl)hydrazono]methyl}-1-pyridiniumyl)-1-butanesulfonate,
4-(2-{[methyl(4-nitrophenyl)hydrazono]methyl}-1-pyridiniumyl)-1-butanesulfonate,
4-{4-[(phenylhydrazono)methyl]-1-pyridiniumyl}-1-butanesulfonate,
4-{3-[(phenylhydrazono)methyl]-1-pyridiniumyl}-1-butanesulfonate,
4-{2-[(phenylhydrazono)methyl]-1-pyridiniumyl}-1-butanesulfonate,
4-(4-{[(4-methoxyphenyl)hydrazono]methyl}-1-pyridiniumyl)-1-butanesulfonate,
4-(3-{[(4-methoxyphenyl)hydrazono]methyl}-1-pyridiniumyl)-1-butanesulfonate,
4-(2-{[(4-methoxyphenyl)hydrazono]methyl}-1-pyridiniumyl)-1-butanesulfonate,
4-{4-[N-methyl-N-phenylethanehydrazonoyl]-1-pyridiniumyl}-1-butanesulfonate,
4-{3-[N-methyl-N-phenylethanehydrazonoyl]-1-pyridiniumyl}-1-butanesulfonate,
4-{2-[N-methyl-N-phenylethanehydrazonoyl]-1-pyridiniumyl}-1-butanesulfonate,
4-{4-[N-phenylethanehydrazonoyl]-1-pyridiniumyl}-1-butanesulfonate,
4-{3-[N-phenylethanehydrazonoyl]-1-pyridiniumyl}-1-butanesulfonate,
4-{2-[N-phenylethanehydrazonoyl]-1-pyridiniumyl}-1-butanesulfonate,
4-(2-{[methyl(phenyl)hydrazono]methyl}-1,3-thiazol-3-ium-3-yl)-1-butanesulfonate,
4-(1-methyl-2-{[methyl(phenyl)hydrazono]methyl}-1H-imidazol-3-ium-3-yl)-1-butanesulfonate,
4-(2-{[methyl(phenyl)hydrazono]methyl}-1,3-oxazol-3-ium-3-yl)-1-butanesulfonate,
4-(4-methyl-5-{[methyl(phenyl)hydrazono]methyl}-4H-1,2,4-triazol-1-ium-1-yl)-1-butanesulfonate,
4-(4-{[methyl(phenyl)hydrazono]methyl}-1-quinoliniumyl)-1-butanesulfonate,
4-(2-{[methyl(phenyl)hydrazono]methyl}-1-quinoliniumyl)-1-butanesulfonate,
4-{4-[(2,3-dihydro-1H-indol-1-ylimino)methyl]-1-pyridiniumyl}-1-butanesulfonate,
4-(4-{[(2,2,3,3-tetramethyl-2,3-dihydro-1H-indol-1-yl)imino]methyl}-1-pyridiniumyl)-1-butanesulfonate,
4-(3,3-dimethyl-2-{[methyl(phenyl)hydrazono]methyl}-3H-indolium-1-yl)-1-butanesulfonate,
4-(2-{[(4-methoxyphenyl)(methyl)hydrazono]methyl}-3,3-dimethyl-3H-indolium-1-yl)-1-butanesulfonate,
4-(3-methyl-6-{[methyl(phenyl)hydrazono]methyl}-2-oxo-2,3-dihydropyrimidin-1-ium-1-yl)-1-butanesulfonate,
4-(1-methyl-7-{[methyl(phenyl)hydrazono]methyl}-1H-indazol-2-ium-2-yl)-1-butanesulfonate,
3-(4-{[methyl(phenyl)hydrazono]methyl}-1-pyridiniumyl)-1-propanesulfonate,
3-(3-{[methyl(phenyl)hydrazono]methyl}-1-pyridiniumyl)-1-propanesulfonate,
3-(2-{[methyl(phenyl)hydrazono]methyl}-1-pyridiniumyl)-1-propanesulfonate,
3-(4-{[(4-methoxyphenyl)(methyl)hydrazono]methyl}-1-pyridiniumyl)-1-propanesulfonate,
3-(3-{[(4-methoxyphenyl)(methyl)hydrazono]methyl}-1-pyridiniumyl)-1-propanesulfonate,
3-(2-{[(4-methoxyphenyl)(methyl)hydrazono]methyl}-1-pyridiniumyl)-1-propanesulfonate,
3-(4-{[(2-methoxyphenyl)(methyl)hydrazono]methyl}-1-pyridiniumyl)-1-propanesulfonate,
3-(3-{[(2-methoxyphenyl)(methyl)hydrazono]methyl}-1-pyridiniumyl)-1-propanesulfonate,
3-(2-{[(2-methoxyphenyl)(methyl)hydrazono]methyl}-1-pyridiniumyl)-1-propanesulfonate,
3-(4-{[(4-hydroxyphenyl)(methyl)hydrazono]methyl}-1-pyridiniumyl)-1-propanesulfonate,
3-(3-{[(4-hydroxyphenyl)(methyl)hydrazono]methyl}-1-pyridiniumyl)-1-propanesulfonate,
3-(2-{[(4-hydroxyphenyl)(methyl)hydrazono]methyl}-1-pyridiniumyl)-1-propanesulfonate,
3-(4-{[methyl(4-methylphenyl)hydrazono]methyl}-1-pyridiniumyl)-1-propanesulfonate,
3-(3-{[methyl(4-methylphenyl)hydrazono]methyl}-1-pyridiniumyl)-1-propanesulfonate,
3-(2-{[methyl(4-methylphenyl)hydrazono]methyl}-1-pyridiniumyl)-1-propanesulfonate,
3-(4-{[(4-chlorophenyl)(methyl)hydrazono]methyl}-1-pyridiniumyl)-1-propanesulfonate,
3-(3-{[(4-chlorophenyl)(methyl)hydrazono]methyl}-1-pyridiniumyl)-1-propanesulfonate, 3-(2-{[(4-chlorophenyl)(methyl)hydrazono]methyl}-1-pyridiniumyl)-1-propanesulfonate,
3-(4-{[methyl(4-nitrophenyl)hydrazono]methyl}-1-pyridiniumyl)-1-propanesulfonate,
3-(3-{[methyl(4-nitrophenyl)hydrazono]methyl}-1-pyridiniumyl)-1-propanesulfonate,
3-(2-{[methyl(4-nitrophenyl)hydrazono]methyl}-1-pyridiniumyl)-1-propanesulfonate,
3-{4-[(phenylhydrazono)methyl]-1-pyridiniumyl}-1-propanesulfonate,
3-{3-[(phenylhydrazono)methyl]-1-pyridiniumyl}-1-propanesulfonate,
3-{2-[(phenylhydrazono)methyl]-1-pyridiniumyl}-1-propanesulfonate,
3-(4-{[(4-methoxyphenyl)hydrazono]methyl}-1-pyridiniumyl)-1-propanesulfonate,
3-(3-{[(4-methoxyphenyl)hydrazono]methyl}-1-pyridiniumyl)-1-propanesulfonate,
3-(2-{[(4-methoxyphenyl)hydrazono]methyl}-1-pyridiniumyl)-1-propanesulfonate,
3-{4-[N-methyl-N-phenylethanehydrazonoyl]-1-pyridiniumyl}-1-propanesulfonate,
3-{3-[N-methyl-N-phenylethanehydrazonoyl]-1-pyridiniumyl}-1-propanesulfonate,
3-{2-[N-methyl-N-phenylethanehydrazonoyl]-1-pyridiniumyl}-1-propanesulfonate,
3-{4-[N-phenylethanehydrazonoyl]-1-pyridiniumyl}-1-propanesulfonate,
3-{3-[N-phenylethanehydrazonoyl]-1-pyridiniumyl}-1-propanesulfonate,
3-{2-[N-phenylethanehydrazonoyl]-1-pyridiniumyl}-1-propanesulfonate,
3-(2-{[methyl(phenyl)hydrazono]methyl}-1,3-thiazol-3-ium-3-yl)-1-propanesulfonate,
3-(1-methyl-2-{[methyl(phenyl)hydrazono]methyl}-1H-imidazol-3-ium-3-yl)-1-propanesulfonate,
3-(2-{[methyl(phenyl)hydrazono]methyl}-1,3-oxazol-3-ium-3-yl)-1-propanesulfonate,
3-(4-methyl-5-{[methyl(phenyl)hydrazono]methyl}-4H-1,2,4-triazol-1-ium-1-yl)-1-propanesulfonate,
3-(4-{[methyl(phenyl)hydrazono]methyl}-1-quinoliniumyl)-1-propanesulfonate,
3-(2-{[methyl(phenyl)hydrazono]methyl}-1-quinoliniumyl)-1-propanesulfonate,
3-{4-[(2,3-dihydro-1H-indol-1-ylimino)methyl]-1-pyridiniumyl}-1-propanesulfonate
3-(4-{[(2,2,3,3-tetramethyl-2,3-dihydro-1H-indol-1-yl)imino]methyl}-1-pyridiniumyl)-1-propanesulfonate,
3-(3,3-dimethyl-2-{[methyl(phenyl)hydrazono]methyl}-3H-indolium-1-yl)-1-propanesulfonate,
3-(2-{[(4-methoxyphenyl)(methyl)hydrazono]methyl}-3,3-dimethyl-3H-indolium-1-yl)-1-propanesulfonate,
3-(3-methyl-6-{[methyl(phenyl)hydrazonol]methyl}-2-oxo-2,3-dihydropyrimidin-1-ium-1-yl)-1-propanesulfonate,
3-(1-methyl-7-{[methyl(phenyl)hydrazono]methyl}-1H-indazol-2-ium-2-yl)-1-propanesulfonate,
4-(4-{[(3-methyl-1,3-benzothiazol-2(3H)-ylidene)hydrazono]methy}-1-pyridiniumyl)-1-butanesulfonate,
4-(3-{[(3-methyl-1,3-benzothiazol-2(3H)-ylidene)hydrazono]methyl}-1-pyridiniumyl)-1-butanesulfonate,
4-(4-{[(3,4-dimethyl-1,3-thiazol-2(3H)-ylidene)hydrazono]methyl}-1-pyridiniumyl)-1-butanesulfonate,
4-(3-{[(3,4-dimethyl-1,3-thiazol-2(3H)-ylidene)hydrazono]methyl}-1-pyridiniumyl)-1-butanesulfonate,
4-(4-{[(3,4,5-trimethyl-1,3-thiazol-2(3H)-ylidene)hydrazono]methy}-1-pyridiniumyl)-1-butanesulfonate,
4-(3-{[(3,4,5-trimethyl-1,3-thiazol-2(3H)-ylidene)hydrazono]methyl}-1-pyridiniumyl)-1-butanesulfonate,
4-(1-methyl-2-{[2-(3-methyl-1,3-benzothiazol-2(3H)-ylidene)hydrazono]methy}-1H-imidazol-3-ium-3-yl)-1-butanesulfonate,
4-(2-{[2-(3,4-dimethyl-1,3-thiazol-2(3H)-ylidene)hydrazono]methy}-1-methyl-1H-imidazol-3-ium-3-yl)-1-butanesulfonate,
4-(2-{[2-(3,4,5-trimethyl-1,3-thiazol-2(3H)-ylidene)hydrazono]methyl}-1-methyl-1H-imidazol-3-ium-3-yl)-1-butanesulfonate,
4-{4-[({bis[4-(dimethylamino)phenyl]methylene}hydrazono)methyl]-1-pyridiniumyl}-1-butanesulfonate,
4-{3-[({bis[4-(dimethylamino)phenyl]methylene}hydrazono)methyl]-1-pyridiniumyl}-1-butanesulfonate,
4-{4-[(9H-fluoren-9-ylidenehydrazono)methyl]-1-pyridiniumyl}-1-butanesulfonate,
4-{4-[({bis[4-(dimethylamino)phenyl]methylene}hydrazono)methyl]-1-quinoliniumyl}-1-butanesulfonate,
3-(4-{[(3-methyl-1,3-benzothiazol-2(3H)-ylidene)hydrazono]methyl}-1-pyridiniumyl)-1-propanesulfonate,
3-(3-{[(3-methyl-1,3-benzothiazol-2(3H)-ylidene)hydrazono]methyl}-1-pyridiniumyl)-1-propanesulfonate,
3-(4-{[(3,4-dimethyl-1,3-thiazol-2(3H)-ylidene)hydrazono]methyl}-1-pyridiniumyl)-1-propanesulfonate,
3-(3-{[(3,4-dimethyl-1,3-thiazol-2(3H)-ylidene)hydrazono]methyl}-1-pyridiniumyl)-1-propanesulfonate,
3-(4-{[(3,4,5-trimethyl-1,3-thiazol-2(3H)-ylidene)hydrazono]methyl}-1-pyridiniumyl)-1-propanesulfonate,
3-(3-{[(3,4,5-trimethyl-1,3-thiazol-2(3H)-ylidene)hydrazono]methyl}-1-pyridiniumyl)-1-propanesulfonate,
3-(1-methyl-2-{[2-(3-methyl-1,3-benzothiazol-2(3H)-ylidene)hydrazono]methyl}-1H-imidazol-3-ium-3-yl)-1-propanesulfonate,
3-(2-{[2-(3,4-dimethyl-1,3-thiazol-2(3H)-ylidene)hydrazono]methyl}-1-methyl-1H-imidazol-3-ium-3-yl)-1-propanesulfonate,
3-(2-{[2-(3,4,5-trimethyl-1,3-thiazol-2(3H)-ylidene)hydrazono]methyl}-1-methyl-1H-imidazol-3-ium-3-yl)-1-propanesulfonate,
3-{4-[({bis[4-(dimethylamino)phenyl]methylene}hydrazono)methyl]-1-pyridiniumyl}-1-propanesulfonate,
3-{3-[({bis[4-(dimethylamino)phenyl]methylene}hydrazono)methyl]-1-pyridiniumyl}-1-propanesulfonate,
3-{4-[(9H-fluoren-9-ylidenehydrazono)methyl]-1-pyridiniumyl}-1-propanesulfonate and
3-{4-[({bis[4-(dimethylamino)phenyl]methylene}hydrazono)methyl]-1-quinoliniumyl}-1-propanesulfonate.

6. The agent according to claim 1, wherein the zwitterionic azomethine dye of the formula (I), (II), or (III) is present in an amount of from about 0.01% to about 10% by weight.

7. The agent according to claim 1, additionally comprising at least one direct dye which is selected from the group consisting of nitro dyes, azo dyes, anthraquinone dyes, triphenylmethane dyes, basic dyes and acidic dyes.

8. The agent according to claim 7, wherein the additional direct dye is present in a total amount of from about 0.01% to about 15% by weight.

9. The agent according to claim 2, wherein in the formula (I), (II), and (III) R13 is hydrogen and n is 2 or 3.

10. The agent according to claim 2, wherein the zwitterionic azomethine dye of the formula (I), (II), or (III) is selected from the group consisting of 4-(4-{[methyl(phenyl)hydrazono]methyl}-1-pyridiniumyl)-1-butanesulfonate,
4-(3-{[methyl(phenyl)hydrazono]methyl}-1-pyridiniumyl)-1-butanesulfonate,
4-(2-{[methyl(phenyl)hydrazono]methyl}-1-pyridiniumyl)-1-butanesulfonate,
4-(4-{[(4-methoxyphenyl)(methyl)hydrazono]methyl}-1-pyridiniumyl)-1-butanesulfonate,
4-(3-{[(4-methoxyphenyl)(methyl)hydrazono]methyl}-1-pyridiniumyl)-1-butanesulfonate,
4-(2-{[(4-methoxyphenyl)(methyl)hydrazono]methyl}-1-pyridiniumyl)-1-butanesulfonate,
4-(4-{[(2-methoxyphenyl)(methyl)hydrazono]methyl}-1-pyridiniumyl)-1-butanesulfonate,
4-(3-{[(2-methoxyphenyl)(methyl)hydrazono]methyl}-1-pyridiniumyl)-1-butanesulfonate,
4-(2-{[(2-methoxyphenyl)(methyl)hydrazono]methyl}-1-pyridiniumyl)-1-butanesulfonate,
4-(4-{[(4-hydroxyphenyl)(methyl)hydrazono]methyl}-1-pyridiniumyl)-1-butanesulfonate,
4-(3-{[(4-hydroxyphenyl)(methyl)hydrazono]methyl}-1-pyridiniumyl)-1-butanesulfonate,
4-(2-{[(4-hydroxyphenyl)(methyl)hydrazono]methyl}-1-pyridiniumyl)-1-butanesulfonate,
4-(4-{[methyl(4-methylphenyl)hydrazono]methyl}-1-pyridiniumyl)-1-butanesulfonate,
4-(3-{[methyl(4-methylphenyl)hydrazono]methyl}-1-pyridiniumyl)-1-butanesulfonate,
4-(2-{[methyl(4-methylphenyl)hydrazono]methyl}-1-pyridiniumyl)-1-butanesulfonate,
4-(4-{[(4-chlorophenyl)(methyl)hydrazono]methyl}-1-pyridiniumyl)-1-butanesulfonate,
4-(3-{[(4-chlorophenyl)(methyl)hydrazono]methyl}-1-pyridiniumyl)-1-butanesulfonate,
4-(2-{[(4-chlorophenyl)(methyl)hydrazono]methyl}-1-pyridiniumyl)-1-butanesulfonate,
4-(4-{[methyl(4-nitrophenyl)hydrazono]methyl}-1-pyridiniumyl)-1-butanesulfonate,
4-(3-{[methyl(4-nitrophenyl)hydrazono]methyl}-1-pyridiniumyl)-1-butanesulfonate,
4-(2-{[methyl(4-nitrophenyl)hydrazono]methyl}-1-pyridiniumyl)-1-butanesulfonate,
4-{4-[(phenylhydrazono)methyl]-1-pyridiniumyl}-1-butanesulfonate,
4-{3-[(phenylhydrazono)methyl]-1-pyridiniumyl}-1-butanesulfonate,
4-{2-[(phenylhydrazono)methyl]-1-pyridiniumyl}-1-butanesulfonate,
4-(4-{[(4-methoxyphenyl)hydrazono]methyl}-1-pyridiniumyl)-1-butanesulfonate,
4-(3-{[(4-methoxyphenyl)hydrazono]methyl}-1-pyridiniumyl)-1-butanesulfonate,
4-(2-{[(4-methoxyphenyl)hydrazono]methyl}-1-pyridiniumyl)-1-butanesulfonate,
4-{4-[N-methyl-N-phenylethanehydrazonoyl]-1-pyridiniumyl}-1-butanesulfonate,
4-{3-[N-methyl-N-phenylethanehydrazonoyl]-1-pyridiniumyl}-1-butanesulfonate,
4-{2-[N-methyl-N-phenylethanehydrazonoyl]-1-pyridiniumyl}-1-butanesulfonate,
4-{4-[N-phenylethanehydrazonoyl]-1-pyridiniumyl}-1-butanesulfonate,
4-{3-[N-phenylethanehydrazonoyl]-1-pyridiniumyl}-1-butanesulfonate,
4-{2-[N-phenylethanehydrazonoyl]-1-pyridiniumyl}-1-butanesulfonate,
4-(2-{[methyl(phenyl)hydrazono]methyl}-1,3-thiazol-3-ium-3-yl)-1-butanesulfonate,
4-(1-methyl-2-{[methyl(phenyl)hydrazono]methyl}-1H-imidazol-3-ium-3-yl)-1-butanesulfonate,
4-(2-{[methyl(phenyl)hydrazono]methyl}-1,3-oxazol-3-ium-3-yl)-1-butanesulfonate,
4-(4-methyl-5-{[methyl(phenyl)hydrazono]methyl}-4H-1,2,4-triazol-1-ium-1-yl)-1-butanesulfonate,
4-(4-{[methyl(phenyl)hydrazono]methyl}-1-quinoliniumyl)-1-butanesulfonate,
4-(2-{[methyl(phenyl)hydrazono]methyl}-1-quinoliniumyl)-1-butanesulfonate,
4-{4-[(2,3-dihydro-1H-indol-1-ylimino)methyl]-1-pyridiniumyl}-1-butanesulfonate,
4-(4-{[(2,2,3,3-tetramethyl-2,3-dihydro-1H-indol-1-yl)imino]methyl}-1-pyridiniumyl)-1-butanesulfonate,
4-(3,3-dimethyl-2-{[methyl(phenyl)hydrazono]methyl}-3H-indolium-1-yl)-1-butanesulfonate,
4-(2-{[(4-methoxyphenyl)(methyl)hydrazono]methyl}-3,3-dimethyl-3H-indolium-1-yl)-1-butanesulfonate,
4-(3-methyl-6-{[methyl(phenyl)hydrazono]methyl}-2-oxo-2,3-dihydropyrimidin-1-ium-1-yl)-1-butanesulfonate,
4-(1-methyl-7-{[methyl(phenyl)hydrazono]methyl}-1H-indazol-2-ium-2-yl)-1-butanesulfonate,
3-(4-{[methyl(phenyl)hydrazono]methyl}-1-pyridiniumyl)-1-propanesulfonate,
3-(3-{[methyl(phenyl)hydrazono]methyl}-1-pyridiniumyl)-1-propanesulfonate,
3-(2-{[methyl(phenyl)hydrazono]methyl}-1-pyridiniumyl)-1-propanesulfonate,
3-(4-{[(4-methoxyphenyl)(methyl)hydrazono]methyl}-1-pyridiniumyl)-1-propanesulfonate,
3-(3-{[(4-methoxyphenyl)(methyl)hydrazono]methyl}-1-pyridiniumyl)-1-propanesulfonate,
3-(2-{[(4-methoxyphenyl)(methyl)hydrazono]methyl}-1-pyridiniumyl)-1-propanesulfonate,
3-(4-{[(2-methoxyphenyl)(methyl)hydrazono]methyl}-1-pyridiniumyl)-1-propanesulfonate,
3-(3-{[(2-methoxyphenyl)(methyl)hydrazono]methyl}-1-pyridiniumyl)-1-propanesulfonate,
3-(2-{[(2-methoxyphenyl)(methyl)hydrazono]methyl}-1-pyridiniumyl)-1-propanesulfonate,
3-(4-{[(4-hydroxyphenyl)(methyl)hydrazono]methyl}-1-pyridiniumyl)-1-propanesulfonate,
3-(3-{[(4-hydroxyphenyl)(methyl)hydrazono]methyl}-1-pyridiniumyl)-1-propanesulfonate,
3-(2-{[(4-hydroxyphenyl)(methyl)hydrazono]methyl}-1-pyridiniumyl)-1-propanesulfonate,
3-(4-{[methyl(4-methylphenyl)hydrazono]methyl}-1-pyridiniumyl)-1-propanesulfonate,
3-(3-{[methyl(4-methylphenyl)hydrazono]methyl}-1-pyridiniumyl)-1-propanesulfonate,
3-(2-{[methyl(4-methylphenyl)hydrazono]methyl}-1-pyridiniumyl)-1-propanesulfonate,
3-(4-{[(4-chlorophenyl)(methyl)hydrazono]methyl}-1-pyridiniumyl)-1-propanesulfonate,
3-(3-{[(4-chlorophenyl)(methyl)hydrazono]methyl}-1-pyridiniumyl)-1-propanesulfonate,
3-(2-{[(4-chlorophenyl)(methyl)hydrazono]methyl}-1-pyridiniumyl)-1-propanesulfonate,
3-(4-{[methyl(4-nitrophenyl)hydrazono]methyl}-1-pyridiniumyl)-1-propanesulfonate,
3-(3-{[methyl(4-nitrophenyl)hydrazono]methyl}-1-pyridiniumyl)-1-propanesulfonate, 3-(2-{[methyl(4-nitrophenyl)hydrazono]methyl}-1-pyridiniumyl)-1-propanesulfonate,
3-{4-[(phenylhydrazono)methyl]-1-pyridiniumyl}-1-propanesulfonate,
3-{3-[(phenylhydrazono)methyl]-1-pyridiniumyl}-1-propanesulfonate,
3-{2-[(phenylhydrazono)methyl]-1-pyridiniumyl}-1-propanesulfonate,
3-(4-{[(4-methoxyphenyl)hydrazono]methyl}-1-pyridiniumyl)-1-propanesulfonate,
3-(3-{[(4-methoxyphenyl)hydrazono]methyl}-1-pyridiniumyl)-1-propanesulfonate,
3-(2-{[(4-methoxyphenyl)hydrazono]methyl}-1-pyridiniumyl)-1-propanesulfonate,
3-{4-[N-methyl-N-phenylethanehydrazonoyl]-1-pyridiniumyl}-1-propanesulfonate,
3-{3-[N-methyl-N-phenylethanehydrazonoyl]-1-pyridiniumyl}-1-propanesulfonate,
3-{2-[N-methyl-N-phenylethanehydrazonoyl]-1-pyridiniumyl}-1-propanesulfonate,
3-{4-[N-phenylethanehydrazonoyl]-1-pyridiniumyl}-1-propanesulfonate,
3-{3-[N-phenylethanehydrazonoyl]-1-pyridiniumyl}-1-propanesulfonate,
3-{2-[N-phenylethanehydrazonoyl]-1-pyridiniumyl}-1-propanesulfonate,
3-(2-{[methyl(phenyl)hydrazono]methyl}-1,3-thiazol-3-ium-3-yl)-1-propanesulfonate,
3-(1-methyl-2-{[methyl(phenyl)hydrazono]methyl}-1H-imidazol-3-ium-3-yl)-1-propanesulfonate,
3-(2-{[methyl(phenyl)hydrazono]methyl}-1,3-oxazol-3-ium-3-yl)-1-propanesulfonate,
3-(4-methyl-5-{[methyl(phenyl)hydrazono]methyl}-4H-1,2,4-triazol-1-ium-1-yl)-1-propanesulfonate,
3-(4-{[methyl(phenyl)hydrazono]methyl}-1-quinoliniumyl)-1-propanesulfonate,
3-(2-{[methyl(phenyl)hydrazono]methyl}-1-quinoliniumyl)-1-propanesulfonate,
3-{4-[(2,3-dihydro-1H-indol-1-ylimino)methyl]-1-pyridiniumyl}-1-propanesulfonate
3-(4-{[(2,2,3,3-tetramethyl-2,3-dihydro-1H-indol-1-yl)imino]methyl}-1-pyridiniumyl)-1-propanesulfonate,
3-(3,3-dimethyl-2-{[methyl(phenyl)hydrazono]methyl}-3H-indolium-1-yl)-1-propanesulfonate,
3-(2-{[(4-methoxyphenyl)(methyl)hydrazono]methyl}-3,3-dimethyl-3H-indolium-1-yl)-1-propanesulfonate,
3-(3-methyl-6-{[methyl(phenyl)hydrazono]methyl}-2-oxo-2,3-dihydropyrimidin-1-ium-1-yl)-1-propanesulfonate,
3-(1-methyl-7-{[methyl(phenyl)hydrazono]methyl}-1H-indazol-2-ium-2-yl)-1-propanesulfonate,
4-(4-{[(3-methyl-1,3-benzothiazol-2(3H)-ylidene)hydrazono]methyl}-1-pyridiniumyl)-1-butanesulfonate,
4-(3-{[(3-methyl-1,3-benzothiazol-2(3H)-ylidene)hydrazono]methyl}-1-pyridiniumyl)-1-butanesulfonate,
4-(4-{[(3,4-dimethyl-1,3-thiazol-2(3H)-ylidene)hydrazono]methyl}-1-pyridiniumyl)-1-butanesulfonate,
4-(3-{[(3,4-dimethyl-1,3-thiazol-2(3H)-ylidene)hydrazono]methyl}-1-pyridiniumyl)-1-butanesulfonate,
4-(4-{[(3,4,5-trimethyl-1,3-thiazol-2(3H)-ylidene)hydrazono]methyl}-1-pyridiniumyl)-1-butanesulfonate,
4-(3-{[(3,4,5-trimethyl-1,3-thiazol-2(3H)-ylidene)hydrazono]methyl}-1-pyridiniumyl)-1-butanesulfonate,
4-1-methyl-2-{[2-(3-methyl-1,3-benzothiazol-2(3H)-ylidene)hydrazono]methyl}-1H-imidazol-3-ium-3-yl)-1-butanesulfonate,
4-(2-{[2-(3,4-dimethyl-1,3-thiazol-2(3H)-ylidene)hydrazono]methyl}-1H-imidazol-3-ium-3-yl)-1-butanesulfonate,
4-(2-{[2-(3,4,5-trimethyl-1,3-thiazol-2(3H)-ylidene)hydrazono]methyl}-1-methyl-1H-imidazol-3-ium-3-yl)-1-butanesulfonate,
4-{4-[({bis[4-(dimethylamino)phenyl]methylene}hydrazono)methyl]-1-pyridiniumyl}-1-butanesulfonate,
4-{3-[({bis[4-(dimethylamino)phenyl]methylene}hydrazono)methyl]-1-pyridiniumyl}-1-butanesulfonate,
4-{4-[(9H-fluoren-9-ylidenehydrazono)methyl]-1-pyridiniumyl}-1-butanesulfonate,
4-{4-[({bis[4-(dimethylamino)phenyl]methylene}hydrazono)methyl]-1-quinoliniumyl}-1-butanesulfonate,
3-(4-{[(3-methyl-1,3-benzothiazol-2(3H)-ylidene)hydrazono]methyl}-1-pyridiniumyl)-1-propanesulfonate,
3-(3-{[(3-methyl-1,3-benzothiazol-2(3H)-ylidene)hydrazono]methyl}-1-pyridiniumyl)-1-propanesulfonate,
3-(4-{[(3,4-dimethyl-1,3-thiazol-2(3H)-ylidene)hydrazono]methyl}-1-pyridiniumyl)-1-propanesulfonate,
3-(3-{[(3,4-dimethyl-1,3-thiazol-2(3H)-ylidene)hydrazono]methyl}-1-pyridiniumyl)-1-propanesulfonate,
3-(4-{[(3,4,5-trimethyl-1,3-thiazol-2(3H)-ylidene)hydrazono]methyl}-1-pyridiniumyl)-1-propanesulfonate,
3-(3-{[(3,4,5-trimethyl-1,3-thiazol-2(3H)-ylidene)hydrazono]methyl}-1-pyridiniumyl)-1-propanesulfonate,
3-(1-methyl-2-{[2-(3-methyl-1,3-benzothiazol-2(3H)-ylidene)hydrazono]methyl}-1H-imidazol-3-ium-3-yl)-1-propanesulfonate,
3-(2-{[2-(3,4-dimethyl-1,3-thiazol-2(3H)-ylidene)hydrazono]methyl}-1-methyl-1H-imidazol-3-ium-3-yl)-1-propanesulfonate,
3-(2-{[2-(3,4,5-trimethyl-1,3-thiazol-2(3H)-ylidene)hydrazono]methyl}-1-methyl-1H-imidazol-3-ium-3-yl)-1-propanesulfonate,
3-{4-[({bis[4-(dimethylamino)phenyl]methylene}hydrazono)methyl]-1-pyridiniumyl}-1-propanesulfonate,
3-{3-[({bis[4-(dimethylamino)phenyl]methylene}hydrazono)methyl]-1-pyridiniumyl}-1-propanesulfonate,
3-{4-[(9H-fluoren-9-ylidenehydrazono)methyl]-1-pyridiniumyl}-1-propanesulfonate and
3-{4-[({bis[4-(dimethylamino)phenyl]methylene}hydrazono)methyl]-1-quinoliniumyl}-1-propanesulfonate.

11. The agent according to claim 2, wherein the zwitterionic azomethine dye of the formula (I), (II), or (III) is present in an amount of from about 0.01% to about 10% by weight.

12. The agent according to claim 3, wherein in the formula (I), (II), and (III) R13 is hydrogen and n is 2 or 3.

13. The agent according to claim 3, wherein the zwitterionic azomethine dye of the formula (I), (II), or (III) is selected from the group consisting of
4-(4-{[methyl(phenyl)hydrazono]methyl}-1-pyridiniumyl)-1-butanesulfonate,
4-(3-{[methyl(phenyl)hydrazono]methyl}-1-pyridiniumyl)-1-butanesulfonate,
4-(2-{[methyl(phenyl)hydrazono]methyl}-1-pyridiniumyl)-1-butanesulfonate,
4-(4-{[(4-methoxyphenyl)(methyl)hydrazono]methyl}-1-pyridiniumyl)-1-butanesulfonate,
4-(3-{[(4-methoxyphenyl)(methyl)hydrazono]methyl}-1-pyridiniumyl)-1-butanesulfonate, 4-(2-{[(4-methoxyphenyl)(methyl)hydrazono]methyl}-1-pyridiniumyl)-1-butanesulfonate,
4-(4-{[(2-methoxyphenyl)(methyl)hydrazono]methyl}-1-pyridiniumyl)-1-butanesulfonate,
4-(3-{[(2-methoxyphenyl)(methyl)hydrazono]methyl}-1-pyridiniumyl)-1-butanesulfonate,
4-(2-{[(2-methoxyphenyl)(methyl)hydrazono]methyl}-1-pyridiniumyl)-1-butanesulfonate,
4-(4-{[(4-hydroxyphenyl)(methyl)hydrazono]methyl}-1-pyridiniumyl)-1-butanesulfonate,
4-(3-{[(4-hydroxyphenyl)(methyl)hydrazono]methyl}-1-pyridiniumyl)-1-butanesulfonate,
4-(2-{[(4-hydroxyphenyl)(methyl)hydrazono]methyl}-1-pyridiniumyl)-1-butanesulfonate,
4-(4-{[methyl(4-methylphenyl)hydrazono]methyl}-1-pyridiniumyl)-1-butanesulfonate,
4-(3-{[methyl(4-methylphenyl)hydrazono]methyl}-1-pyridiniumyl)-1-butanesulfonate,
4-(2-{[methyl(4-methylphenyl)hydrazono]methyl}-1-pyridiniumyl)-1-butanesulfonate,
4-(4-{[(4-chlorophenyl)(methyl)hydrazono]methyl}-1-pyridiniumyl)-1-butanesulfonate,
4-(3-{[(4-chlorophenyl)(methyl)hydrazono]methyl}-1-pyridiniumyl)-1-butanesulfonate,
4-(2-{[(4-chlorophenyl)(methyl)hydrazono]methyl}-1-pyridiniumyl)-1-butanesulfonate,
4-(4-{[methyl(4-nitrophenyl)hydrazono]methyl}-1-pyridiniumyl)-1-butanesulfonate,
4-(3-{[methyl(4-nitrophenyl)hydrazono]methyl}-1-pyridiniumyl)-1-butanesulfonate,
4-(2-{[methyl(4-nitrophenyl)hydrazono]methyl}-1-pyridiniumyl)-1-butanesulfonate,
4-{4-[(phenylhydrazono)methyl]-1-pyridiniumyl}-1-butanesulfonate,
4-{3-[(phenylhydrazono)methyl]-1-pyridiniumyl}-1-butanesulfonate,
4-{2-[(phenylhydrazono)methyl]-1-pyridiniumyl}-1-butanesulfonate,
4-(4-{[(4-methoxyphenyl)hydrazono]methyl}-1-pyridiniumyl)-1-butanesulfonate,
4-(3-{[(4-methoxyphenyl)hydrazono]methyl}-1-pyridiniumyl)-1-butanesulfonate,
4-(2-{[(4-methoxyphenyl)hydrazono]methyl}-1-pyridiniumyl)-1-butanesulfonate,
4-{4-[N-methyl-N-phenylethanehydrazonoyl]-1-pyridiniumyl}-1-butanesulfonate,
4-{3-[N-methyl-N-phenylethanehydrazonoyl]-1-pyridiniumyl}-1-butanesulfonate,
4-{2-[N-methyl-N-phenylethanehydrazonoyl]1-pyridiniumyl}-1-butanesulfonate,
4-{4-[N-phenylethanehydrazonoyl]-1-pyridiniumyl}-1-butanesulfonate,
4-{3-[N-phenylethanehydrazonoyl]-1-pyridiniumyl}-1-butanesulfonate.
4-{2-[N-phenylethanehydrazonoyl]-1-pyridiniumyl}-1-butanesulfonate,
4-(2-{[methyl(phenyl)hydrazono]methyl}-1,3-thiazol-3-ium-3-yl)-1-butanesulfonate,
4-(1-methyl-2-{[methyl(phenyl)hydrazono]methyl}-1H-imidazol-3-ium-3-yl)-1-butanesulfonate,
4-(2-{[methyl(phenyl)hydrazono]methyl}-1,3-oxazol-3-ium-3-yl)-1-butanesulfonate,
4-(4-methyl-5-{[methyl(phenyl)hydrazono]methyl}-4H-1,2,4-triazol-1-ium-1-yl)-1-butanesulfonate,
4-(4-{[methyl(phenyl)hydrazono]methyl}-1-quinoliniumyl)-1-butanesulfonate,
4-(2-{[methyl(phenyl)hydrazono]methyl}-1-quinoliniumyl)-1-butanesulfonate,
4-{4-[(2,3-dihydro-1H-indol-1-ylimino)methyl]-1-pyridiniumyl}-1-butanesulfonate,
4-(4-{[(2,2,3,3-tetramethyl-2,3-dihydro-1H-indol-1-yl)imino]methyl}-1-pyridiniumyl)-1-butanesulfonate,
4-(3,3-dimethyl-2-{[methyl(phenyl)hydrazono]methyl}-3H-indolium-1-yl)-1-butanesulfonate,
4-(2-{[(4-methoxyphenyl)(methyl)hydrazono]methyl}-3,3-dimethyl-3H-indolium-1-yl)-1-butanesulfonate,
4-(3-methyl-6-{[methyl(phenyl)hydrazono]methyl}-2-oxo-2,3-dihydropyrimidin-1-ium-1-yl)-1-butanesulfonate,
4-(1-methyl-7-{[methyl(phenyl)hydrazono]methyl}-1H-1-indazol-2-ium-2-yl)-1-butanesulfonate,
3-(4-{[methyl(phenyl)hydrazono]methyl}-1-pyridiniumyl)-1-propanesulfonate,
3-(3-{[methyl(phenyl)hydrazono]methyl}-1-pyridiniumyl)-1-propanesulfonate,
3-(2-{[methyl(phenyl)hydrazono]methyl}-1-pyridiniumyl)-1-propanesulfonate,
3-(4-{[(4-methoxyphenyl)(methyl)hydrazono]methyl}-1-pyridiniumyl)-1-propanesulfonate,
3-(3-{[(4-methoxyphenyl)(methyl)hydrazono]methyl}-1-pyridiniumyl)-1-propanesulfonate,
3-(2-{[(4-methoxyphenyl)(methyl)hydrazono]methyl}-1-pyridiniumyl)-1-propanesulfonate,
3-(4-{[(2-methoxyphenyl)(methyl)hydrazono]methyl}-1-pyridiniumyl)-1-propanesulfonate,
3-(3-{[(2-methoxyphenyl)(methyl)hydrazono]methyl}-1-pyridiniumyl)-1-propanesulfonate,
3-(2-{[(2-methoxyphenyl)(methyl)hydrazono]methyl}-1-pyridiniumyl)-1-propanesulfonate,
3-(4-{[(4-hydroxyphenyl)(methyl)hydrazono]methyl}-1-pyridiniumyl)-1-propanesulfonate,
3-(3-{[(4-hydroxyphenyl)(methyl)hydrazono]methyl}-1-pyridiniumyl)-1-propanesulfonate,
3-(2-{[(4-hydroxyphenyl)(methyl)hydrazono]methyl}-1-pyridiniumyl)-1-propanesulfonate,
3-(4-{[methyl(4-methylphenyl)hydrazono]methyl}-1-pyridiniumyl)-1-propanesulfonate,
3-(3-{[methyl(4-methylphenyl)hydrazono]methyl}-1-pyridiniumyl)-1-propanesulfonate,
3-(2-{[methyl(4-methylphenyl)hydrazono]methyl}-1-pyridiniumyl)-1-propanesulfonate,
3-(4-{[(4-chlorophenyl)(methyl)hydrazono]methyl-1-pyridiniumyl)-1-propanesulfonate,
3-(3-{[(4-chlorophenyl)(methyl)hydrazono]methyl}-1-pyridiniumyl)-1-propanesulfonate,
3-(2-{[(4-chlorophenyl)(methyl)hydrazono]methyl}-1-pyridiniumyl)-1-propanesulfonate,
3-(4-{[methyl(4-nitrophenyl)hydrazono]methyl}-1-pyridiniumyl)-1-propanesulfonate,
3-(3-{[methyl(4-nitrophenyl)hydrazono]methyl}-1-pyridiniumyl)-1-propanesulfonate,
3-(2-{[methyl(4-nitrophenyl)hydrazono]methyl}-1-pyridiniumyl)-1-propanesulfonate,
3-{4-[(phenylhydrazono)methyl]-1-pyridiniumyl}-1-propanesulfonate,
3-{3-[(phenylhydrazono)methyl]-1-pyridiniumyl}-1-propanesulfonate,
3-{2-[(phenylhydrazono)methyl]-1-pyridiniumyl}-1-propanesulfonate,
3-(4-{[(4-methoxyphenyl)hydrazono]methyl}-1-pyridiniumyl)-1-propanesulfonate,
3-(3-{[(4-methoxyphenyl)hydrazono]methyl}-1-pyridiniumyl)-1-propanesulfonate, 3-(2-{[(4-methoxyphenyl)hydrazono]methyl}-1-pyridiniumyl)-1-propanesulfonate,
3-{4-[N-methyl-N-phenylethanehydrazonoyl]-1-pyridiniumyl}-1-propanesulfonate,
3-{3-[N-methyl-N-phenylethanehydrazonoyl]-1-pyridiniumyl}-1-propanesulfonate,
3-{2-[N-methyl-N-phenylethanehydrazonoyl]-1-pyridiniumyl}-1-propanesulfonate,
3-{4-[N-phenylethanehydrazonoyl]-1-pyridiniumyl}-1-propanesulfonate,
3-{3-[N-phenylethanehydrazonoyl]-1-pyridiniumyl}-1-propanesulfonate,
3-{2-[N-phenylethanehydrazonoyl]-1-pyridiniumyl}-1-propanesulfonate,
3-(2-{[methyl(phenyl)hydrazono]methyl}-1,3-thiazol-3-ium-3-yl)-1-propanesulfonate,
3-(1-methyl-2-{[methyl(phenyl)hydrazono]methyl}-1H-imidazol-3-ium-3-yl)-1-propanesulfonate,
3-(2-{[methyl(phenyl)hydrazono]methyl}-1,3-oxazol-3-ium-3-yl)-1-propanesulfonate,
3-(4-methyl-5-{[methyl(phenyl)hydrazono]methyl}-4H-1,2,4-triazol-1-ium-1-yl)-1-propanesulfonate,
3-(4-{[methyl(phenyl)hydrazono]methyl}-1-quinoliniumyl)-1-propanesulfonate,
3-(2-{[methyl(phenyl)hydrazono]methyl}-1-quinoliniumyl)-1-propanesulfonate,
3-{4-[(2,3-dihydro-1H-indol-1-ylimino)methyl]-1-pyridiniumyl}-1-propanesulfonate
3-(4-{[(2,2,3,3-tetramethyl-2,3-dihydro-1H-indol-1-yl)imino]methyl}-1-pyridiniumyl)-1-propanesulfonate,
3-(3,3-dimethyl-2-{[methyl(phenyl)hydrazono]methyl}-3H-indolium-1-yl)-1-propanesulfonate,
3-(2-{[(4-methoxyphenyl)(methyl)hydrazono]methyl}-3,3-dimethyl-3H-indolium-1-yl)-1-propanesulfonate,
3-(3-methyl-6-{[methyl(phenyl)hydrazono]methyl}-2-oxo-2,3-dihydropyrimidin-1-ium-1-yl)-1-propanesulfonate,
3-(1-methyl-7-{[methyl(phenyl)hydrazono]methyl}-1H-indazol-2-ium-2-yl)-1-propanesulfonate,
4-(4-{[(3-methyl-1,3-benzothiazol-2(3H)-ylidene)hydrazono]methyl}-1-pyridiniumyl)-1-butanesulfonate,
4-(3-{[(3-methyl-1,3-benzothiazol-2(3H)-ylidene)hydrazono]methyl}-1-pyridiniumyl)-1-butanesulfonate,
4-(4-{[(3,4-dimethyl-1,3-thiazol-2(3H)-ylidene)hydrazono]methyl}-1-pyridiniumyl)-1-butanesulfonate,
4-(3-{[(3,4-dimethyl-1,3-thiazol-2(3H)-ylidene)hydrazono]methyl}-1-pyridiniumyl)-1-butanesulfonate,
4-(4-{[(3,4,5-trimethyl-1,3-thiazol-2(3H)-ylidene)hydrazono]methyl}-1-pyridiniumyl)-1-butanesulfonate,
4-(3-{[(3,4,5-trimethyl-1,3-thiazol-2(3H)-ylidene)hydrazono]methyl}-1-pyridiniumyl)-1-butanesulfonate,
4-(1-methyl-2-{[2-(3-methyl-1,3-benzothiazol-2(3H)-ylidene)hydrazono]methyl}-1H-imidazol-3-ium-3-yl)-1-butanesulfonate,
4-(2-{[2-(3,4-dimethyl-1,3-thiazol-2(3H)-ylidene)hydrazono]methyl}-1-methyl-1H-imidazol-3-ium-3-yl)-1-butanesulfonate,
4-(2-{[2-(3,4,5-trimethyl-1,3-thiazol-2(3H)-ylidene)hydrazono]methyl}-1H-imidazol-3-ium-3-yl)-1-butanesulfonate,
4-{4-[({bis[4-(dimethylamino)phenyl]methylene}hydrazono)methy]-1-pyridiniumyl}-1-butanesulfonate,
4-{3-[({bis[4-(dimethylamino)phenyl]methylene}hydrazono)methyl]-1-pyridiniumyl}-1-butanesulfonate,
4-{4-[(9H-fluoren-9-ylidenehydrazono)methyl}-1-pyridiniumyl}-1-butanesulfonate,
4-{4-[({bis[4-(dimethylamino)phenyl]methylene}hydrazono)methyl]-1-quinoliniumyl}-1-butanesulfonate,
3-(4-{[(3-methyl-1,3-benzothiazol-2(3H)-ylidene)hydrazono]methyl}-1-pyridiniumyl)-1-propanesulfonate,
3-(3-{[(3-methyl-1,3-benzothiazol-2(3H)-ylidene)hydrazono]methyl}-1-pyridiniumyl)-1-propanesulfonate,
3-(4-{[(3,4-dimethyl-1,3-thiazol-2(3H)-ylidene)hydrazono]methyl}-1-pyridiniumyl)-1-propanesulfonate,
3-(3-{[(3,4-dimethyl-1,3-thiazol-2(3H)-ylidene)hydrazono]methyl}-1-pyridiniumyl)-1-propanesulfonate,
3-(4-{[(3,4,5-trimethyl-1,3-thiazol-2(3H)-ylidene)hydrazono]methyl}-1-pyridiniumyl)-1-propanesulfonate,
3-(3-{[(3,4,5-trimethyl-1,3-thiazol-2(3H)-ylidene)hydrazono]methyl}-1-pyridiniumyl)-1-propanesulfonate,
3-(1-methyl-2-{[2-(3-methyl-1,3-benzothiazol-2(3H)-ylidene)hydrazono]methyl}-1H-imidazol-3-ium-3-yl)-1-propanesulfonate,
3-(2-{[2-(3,4-dimethyl-1,3-thiazol-2(3H)-ylidene)hydrazono]methyl}-1-methyl-1H-imidazol-3-ium-3-yl)-1-propanesulfonate,
3-(2-{[2-(3,4,5-trimethyl-1,3-thiazol-2(3H)-ylidene)hydrazono]methyl}-1-methyl-1H-imidazol-3-ium-3-yl)-1-propanesulfonate,
3-{4-[({bis[4-(dimethylamino)phenyl]methylene}hydrazono)methyl]-1-pyridiniumyl}-1-propanesulfonate,
3-{3-[({bis[4-(dimethylamino)phenyl]methylene}hydrazono)methyl]-1-pyridiniumyl}-1-propanesulfonate,
3-{4-[(9H-fluoren-9-ylidenehydrazono)methyl}-1-pyridiniumyl}-1-propanesulfonate and
3-{4-[({bis[4-(dimethylamino)phenyl]methylene}hydrazono)methyl]-1-quinoliniumyl}-1-propanesulfonate.

14. The agent according to claim 3, wherein the zwitterionic azomethine dye of the formula (I), (II), or (III) is present in an amount of from about 0.01% to about 10% by weight.

* * * * *

UNITED STATES PATENT AND TRADEMARK OFFICE
CERTIFICATE OF CORRECTION

| | | |
|---|---|---|
| PATENT NO. | : 7,513,918 B2 | Page 1 of 2 |
| APPLICATION NO. | : 11/788065 | |
| DATED | : April 7, 2009 | |
| INVENTOR(S) | : Cécile Pasquier et al. | |

It is certified that error appears in the above-identified patent and that said Letters Patent is hereby corrected as shown below:

In the Claims;

Column 30, Line 4

Claim 2 insert --to-- after the term "compounds" and before the term "urea".

Column 35, Line 53

Claim 5 delete "hydrazonol" insert --hydrazono--.

Column 35, Line 59

Claim 5 delete "methy" insert --methyl--.

Column 35, Line 67

Claim 5 delete "methy" insert --methyl--.

Column 36, Line 4

Claim 5 delete "methy" insert --methyl--.

Column 36, Line 7

Claim 5 delete "methy" insert --methyl--.

Column 41, Line 35

Claim 13 delete "}" insert --]-- after the term "methyl".

Signed and Sealed this
First Day of March, 2016

Michelle K. Lee
*Director of the United States Patent and Trademark Office*

CERTIFICATE OF CORRECTION (continued)
U.S. Pat. No. 7,513,918 B2

In the claims;

<u>Column 41, Line 55</u>

Claim 13 delete "." insert --,--.

<u>Column 42, Line 15</u>

Claim 13 delete "1-" just prior to the term "indazol".

<u>Column 42, Line 46</u>

Claim 13 delete "}" insert --]-- after the term "methyl".

<u>Column 44, Line 5</u>

Claim 13 delete "methy" insert --methyl--.

<u>Column 44, Line 8</u>

Claim 13 delete "methy" insert --methyl--.